United States Patent
Low et al.

(10) Patent No.: US 11,386,347 B2
(45) Date of Patent: Jul. 12, 2022

(54) SWAP NETWORKS FOR QUANTUM COMPUTATION

(71) Applicant: MICROSOFT TECHNOLOGY LICENSING, LLC, Redmond, WA (US)

(72) Inventors: Guang Hao Low, Redmond, WA (US); Nathan Wiebe, Seattle, WA (US); Natalie M. Klco, Seattle, WA (US); Yuan Su, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 419 days.

(21) Appl. No.: 16/438,409

(22) Filed: Jun. 11, 2019

(65) Prior Publication Data
US 2020/0394544 A1    Dec. 17, 2020

(51) Int. Cl.
*G06N 10/00*   (2022.01)
*G16C 10/00*   (2019.01)
*B82Y 10/00*   (2011.01)

(52) U.S. Cl.
CPC .............. *G06N 10/00* (2019.01); *B82Y 10/00* (2013.01); *G16C 10/00* (2019.02)

(58) Field of Classification Search
CPC ................................ G06N 10/00; B82Y 10/00
See application file for complete search history.

(56) References Cited

FOREIGN PATENT DOCUMENTS

WO    2019077240 A1    4/2019

OTHER PUBLICATIONS

Hirata, et al., "An efficient conversion of quantum circuits to a linear nearest neighbor architecture", In Journal of Quantum Information and Computation, vol. 11, Issue 1 and 2, Jan. 2011, pp. 142-166.
Li, et al., "Tackling the Qubit Mapping Problem for NISQ-Era Quantum Devices", In Repository of arXiv:1809.02573, Sep. 7, 2018, 13 Pages.
Moll, et al., "Quantum optimization using variational algorithms on near-term quantum devices", In Repository of arXiv:1710.01022, Oct. 3, 2017, 30 Pages.

(Continued)

*Primary Examiner* — Matthew L Reames
(74) *Attorney, Agent, or Firm* — Holzer Patel Drennan

(57) ABSTRACT

A quantum computer and methods of operating the quantum computer, such that the quantum computer is enabled to fully simulate molecular chemistry, are described. The circuit depth of the quantum computer is reduced by at least an order of magnitude, as compared to conventional quantum computing methods. Parallelized qubit or fermionic swap networks are employed to render the non-local terms of the second quantized Hamiltonian, as local on consecutive qubits of the computer. Thus, non-local quantum dynamics are rendered local. By localizing the non-local interactions, the quantum computations may be significantly parallelized and a single template circuit, simulating the time-evolution operator for 4-qubit interactions, may be applied to the localized groupings of four qubits. In addition to chemistry, the quantum computer and the methods of operating the quantum computer may be employed to localize any many-body interaction, while reducing the required circuit depth, via parallelizations of the localized computations.

20 Claims, 26 Drawing Sheets

(56) References Cited

OTHER PUBLICATIONS

"International Search Report and Written Opinion Issued in PCT Application No. PCT/US2020/036569", dated Sep. 16, 2020, 12 Pages.

Babbush, et al., "Low Depth Quantum Simulation of Electronic Structure", In Repository of arXiv:1706.00023v3, Jan. 14, 2018, 41 Pages.

Babbush, et al., "Low-Depth Quantum Simulation of Materials", In Journal of Physical Review X, vol. 8, No. 1, Mar. 21, 2018, 40 Pages.

Hastings, et al., "Improving Quantum Algorithms for Quantum Chemistry", In Repository of arXiv:1403.1539v2, Mar. 23, 2014, 12 Pages.

Jones, Cody, "Novel Constructions for the Fault-Tolerant Toffoli Gate", In Repository of arXiv:1212.5069v1, Dec. 20, 2012, 5 Pages.

Kivlichan, et al., "Quantum Simulation of Electronic Structure with Linear Depth and Connectivity", In Journal of Physical Review Letters, vol. 120, No. 11, Mar. 13, 2018, 8 Pages.

Reiher, et al., "Elucidating Reaction Mechanisms on Quantum Computers", In Proceedings of the National Academy at Sciences, vol. 114, Issue 29, Jul. 18, 2017, pp. 7555-7560.

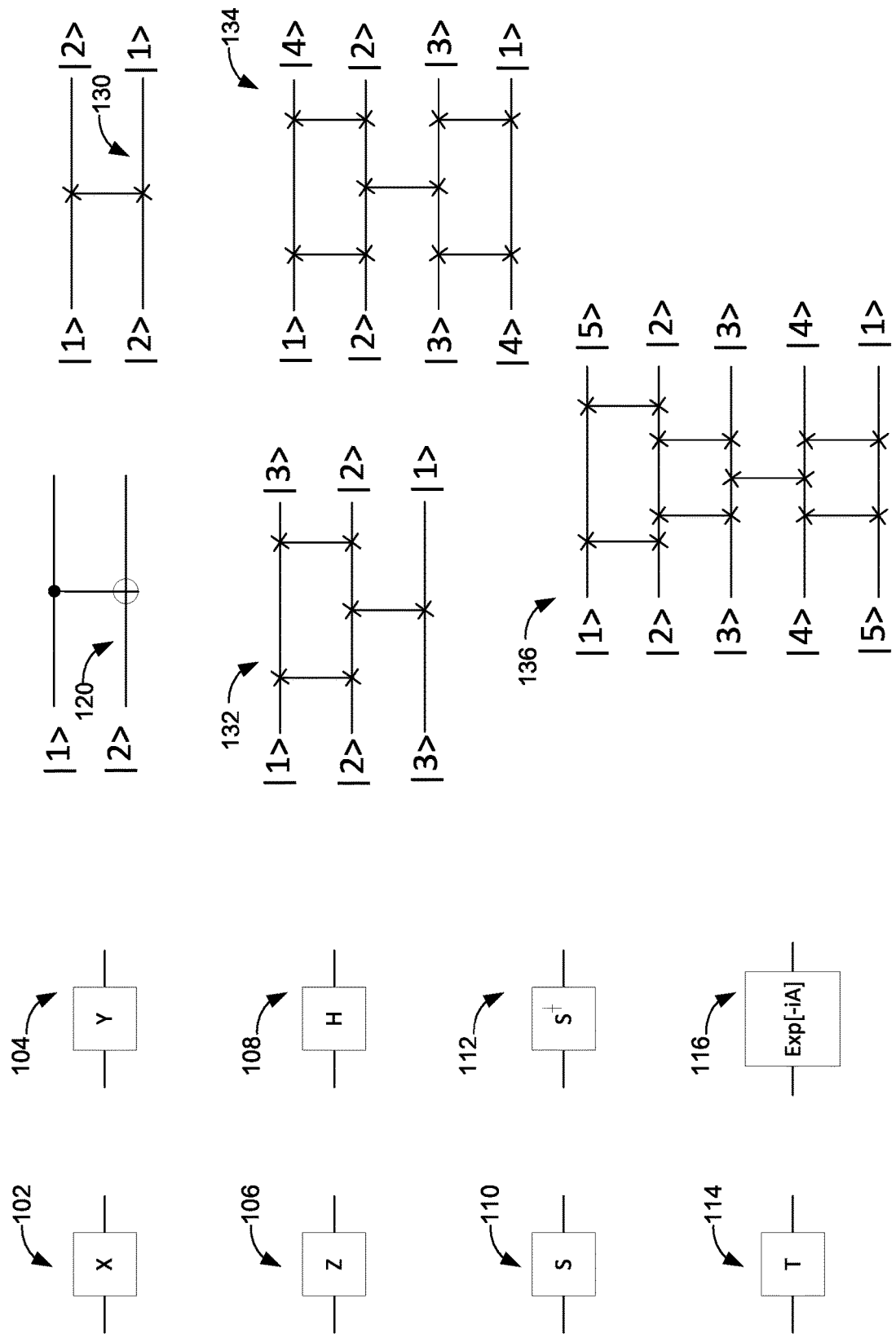

$$e^{-iH_{pqrs}} =\begin{pmatrix} 1 & 0 & 0 & 0 & 0 & 0 & 0 & 0 & 0 & 0 & 0 & 0 & 0 & 0 & 0 & 0 \\ 0 & 1 & 0 & 0 & 0 & 0 & 0 & 0 & 0 & 0 & 0 & 0 & 0 & 0 & 0 & 0 \\ 0 & 0 & 1 & 0 & 0 & 0 & 0 & 0 & 0 & 0 & 0 & 0 & 0 & 0 & 0 & 0 \\ 0 & 0 & 0 & \cos(hq-hs) & 0 & 0 & 0 & 0 & 0 & 0 & 0 & 0 & -i\sin(hq-hs) & 0 & 0 & 0 \\ 0 & 0 & 0 & 0 & 1 & 0 & 0 & 0 & 0 & 0 & 0 & 0 & 0 & 0 & 0 & 0 \\ 0 & 0 & 0 & 0 & 0 & \cos(hq-hr) & 0 & 0 & 0 & -i\sin(hq-hr) & 0 & 0 & 0 & 0 & 0 & 0 \\ 0 & 0 & 0 & 0 & 0 & 0 & \cos(hr-hs) & 0 & i\sin(hr-hs) & 0 & 0 & 0 & 0 & 0 & 0 & 0 \\ 0 & 0 & 0 & 0 & 0 & 0 & 0 & 1 & 0 & 0 & 0 & 0 & 0 & 0 & 0 & 0 \\ 0 & 0 & 0 & 0 & 0 & 0 & i\sin(hr-hs) & 0 & \cos(hr-hs) & 0 & 0 & 0 & 0 & 0 & 0 & 0 \\ 0 & 0 & 0 & 0 & 0 & -i\sin(hq-hr) & 0 & 0 & 0 & \cos(hq-hr) & 0 & 0 & 0 & 0 & 0 & 0 \\ 0 & 0 & 0 & 0 & 0 & 0 & 0 & 0 & 0 & 0 & 1 & 0 & 0 & 0 & 0 & 0 \\ 0 & 0 & 0 & 0 & 0 & 0 & 0 & 0 & 0 & 0 & 0 & \cos(hq-hr) & 0 & 0 & 0 & -i\sin(hq-hr) \\ 0 & 0 & 0 & -i\sin(hq-hs) & 0 & 0 & 0 & 0 & 0 & 0 & 0 & 0 & \cos(hq-hs) & 0 & 0 & 0 \\ 0 & 0 & 0 & 0 & 0 & 0 & 0 & 0 & 0 & 0 & 0 & 0 & 0 & 1 & 0 & 0 \\ 0 & 0 & 0 & 0 & 0 & 0 & 0 & 0 & 0 & 0 & 0 & 0 & 0 & 0 & 1 & 0 \\ 0 & 0 & 0 & 0 & 0 & 0 & 0 & 0 & 0 & 0 & 0 & 0 & 0 & 0 & 0 & 1 \end{pmatrix}$$

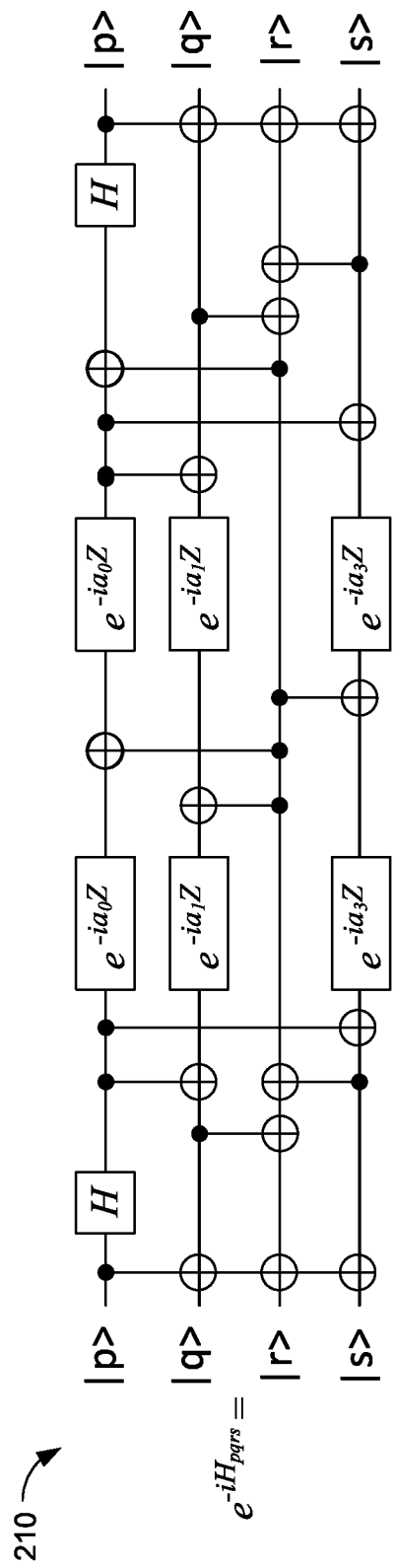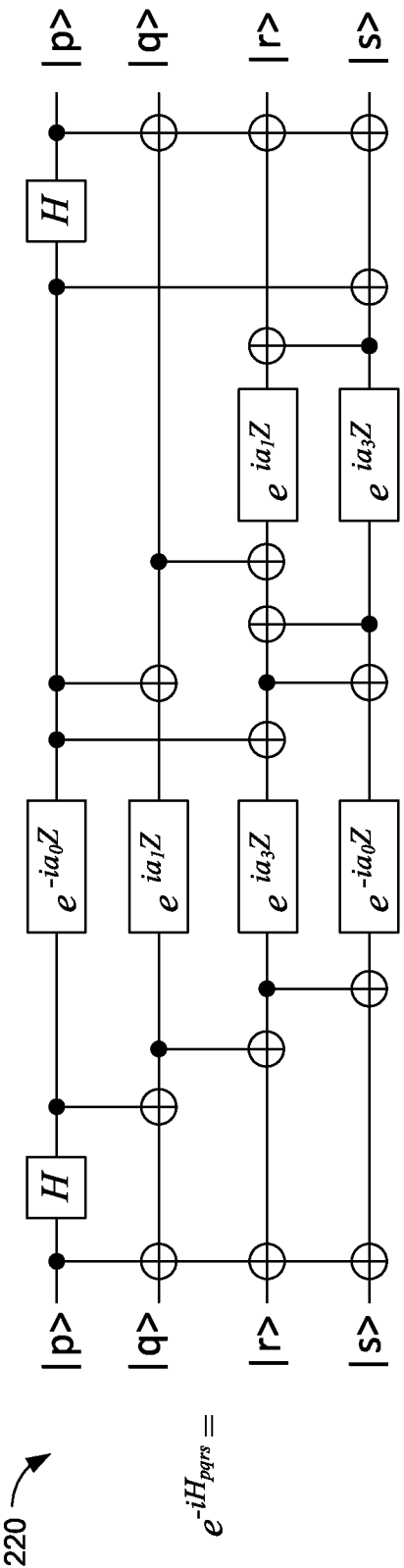

| CATEGORY | MEMBERS | NUMBER | LARGE-N RATIO | DEPTH |
|---|---|---|---|---|
| 0 | 123 | $\binom{N/3}{1}^3$ | $\frac{2}{9} = 22.2\%$ | $d_w(n_1)d_w(n_2)$ |
| 1 | 122,133 | $2 \times \binom{N/3}{1}\binom{N/3}{2}$ | $\frac{2}{9} = 22.2\%$ | $d_w(n_1)d_2(n_2)$ |
| 2 | 211,233 | $2 \times \binom{N/3}{1}\binom{N/3}{2}$ | $\frac{2}{9} = 22.2\%$ | $d_w(n_2)d_2(n_1)$ |
| 3 | 311,322 | $2 \times \binom{N/3}{1}\binom{N/3}{2}$ | $\frac{2}{9} = 22.2\%$ | $d_w(n_3)d_2(n_1)$ |
| 4 | 111,222,333 | $3 \times \binom{N/3}{3}$ | $\frac{1}{9} = 11.1\%$ | |

| N | 0: 123 | 1: 122,133 | 2: 211,233 | 3: 311,322 |
|---|---|---|---|---|
| 5 | 12312 | 12213 | 11232 | 11322 |
| 6 | 123123 | 122133 | 112332 | 113223 |
| 7 | 1231231 | 1221331 | 1121332 | 1131223 |
| 8 | 12312312 | 12212331 | 11213322 | 11312232 |
| 9 | 123123123 | 122123323 | 112133232 | 113122323 |
| 10 | 1231231231 | 1221233131 | 1121133232 | 1131122323 |

| | | | | | | | | Wheel_1 530 | Wheel_2 540 | Wheel_3 560 |
|---|---|---|---|---|---|---|---|---|---|---|
| 1 | 2 | 3 | 4 | 5 | 6 | 7 | 8 | [1,4,7] | [2,5,8] | [3,6] |
| 4 | 2 | 3 | 1 | 5 | 6 | 7 | 8 | [4,1,7] | [2,5,8] | [3,6] |
| 4 | 2 | 3 | 7 | 5 | 6 | 1 | 8 | [4,7,1] | [2,5,8] | [3,6] |
| 7 | 2 | 3 | 4 | 5 | 6 | 1 | 8 | [7,4,1] | [2,5,8] | [3,6] |
| 7 | 2 | 3 | 1 | 5 | 6 | 4 | 8 | [7,1,4] | [2,5,8] | [3,6] |
| 7 | 5 | 3 | 1 | 2 | 6 | 4 | 8 | [7,1,4] | [5,2,8] | [3,6] |
| 1 | 5 | 3 | 7 | 2 | 6 | 4 | 8 | [1,7,4] | [5,2,8] | [3,6] |
| 1 | 5 | 3 | 4 | 2 | 6 | 7 | 8 | [1,4,7] | [5,2,8] | [3,6] |
| 4 | 5 | 3 | 1 | 2 | 6 | 7 | 8 | [4,1,7] | [5,2,8] | [3,6] |
| 4 | 5 | 3 | 7 | 2 | 6 | 1 | 8 | [4,7,1] | [5,2,8] | [3,6] |
| 4 | 5 | 3 | 7 | 8 | 6 | 1 | 2 | [4,7,1] | [5,8,2] | [3,6] |
| 7 | 5 | 3 | 4 | 8 | 6 | 1 | 2 | [7,4,1] | [5,8,2] | [3,6] |
| 7 | 5 | 3 | 1 | 8 | 6 | 4 | 2 | [7,1,4] | [5,8,2] | [3,6] |
| 1 | 5 | 3 | 7 | 8 | 6 | 4 | 2 | [1,7,4] | [5,8,2] | [3,6] |
| 1 | 5 | 3 | 4 | 8 | 6 | 7 | 2 | [1,4,7] | [5,8,2] | [3,6] |
| 1 | 8 | 3 | 4 | 5 | 6 | 7 | 2 | [1,4,7] | [8,5,2] | [3,6] |
| 4 | 8 | 3 | 1 | 5 | 6 | 7 | 2 | [4,1,7] | [8,5,2] | [3,6] |
| 4 | 8 | 3 | 7 | 5 | 6 | 1 | 2 | [4,7,1] | [8,5,2] | [3,6] |
| 7 | 8 | 3 | 4 | 5 | 6 | 1 | 2 | [7,4,1] | [8,5,2] | [3,6] |
| 7 | 8 | 3 | 1 | 5 | 6 | 4 | 2 | [7,1,4] | [8,5,2] | [3,6] |
| 7 | 8 | 3 | 1 | 2 | 6 | 4 | 5 | [7,1,4] | [8,2,5] | [3,6] |
| 1 | 8 | 3 | 7 | 2 | 6 | 4 | 5 | [1,7,4] | [8,2,5] | [3,6] |
| 1 | 8 | 3 | 4 | 2 | 6 | 7 | 5 | [1,4,7] | [8,2,5] | [3,6] |
| 4 | 8 | 3 | 1 | 2 | 6 | 7 | 5 | [4,1,7] | [8,2,5] | [3,6] |
| 4 | 8 | 3 | 7 | 2 | 6 | 1 | 5 | [4,7,1] | [8,2,5] | [3,6] |

*FIG. 5B*

| Category | Members | Number | Large-$n$ ratio | depth |
|---|---|---|---|---|
| 1 | 1234 | $\binom{n/4}{1}^4$ | $\frac{24}{64} = 0.09375$ | $d_w(n_1)d_w(n_2)d_w(n_3)d_w(n_4)$ |
| 2 | 1122, 3344 | $2 \times \binom{n/4}{2}^2$ | $\frac{3}{64} = 0.046875$ | $d_2(n_1)d_s(\lceil n_2/2 \rceil)(2d_w(\lceil n_2/2 \rceil) - 1)$ |
| 3 | 1133, 2244 | $2 \times \binom{n/4}{2}^2$ | $\frac{3}{64} = 0.046875$ | $d_2(n_1)d_s(\lceil n_3/2 \rceil)(2d_w(\lceil n_3/2 \rceil) - 1)$ |
| 4 | 1144, 2233 | $2 \times \binom{n/4}{2}^2$ | $\frac{3}{64} = 0.046875$ | $\max\{d_2(n_1)d_s(n_4)(2d_w(\lceil n_4/2 \rceil) - 1),$ $d_2(n_2)d_s(\lceil n_3/2 \rceil)(2d_w(\lceil n_3/2 \rceil) - 1)\}$ |
| 5 | 1134, 2234 | $2 \times \binom{n/4}{2}\binom{n/4}{1}^2$ | $\frac{6}{64} = 0.09375$ | $d_2(n_1)d_w(n_3)d_w(n_4)$ |
| 6 | 1124, 3324 | $2 \times \binom{n/4}{2}\binom{n/4}{1}^2$ | $\frac{6}{64} = 0.09375$ | $d_2(n_1)d_w(n_2)d_w(n_4)$ |
| 7 | 1123, 4423 | $2 \times \binom{n/4}{2}\binom{n/4}{1}^2$ | $\frac{6}{64} = 0.09375$ | $d_2(n_1)d_w(n_2)d_w(n_3)$ |
| 8 | 2214, 3314 | $2 \times \binom{n/4}{2}\binom{n/4}{1}^2$ | $\frac{6}{64} = 0.09375$ | $d_2(n_2)d_w(n_1)d_w(n_4)$ |
| 9 | 2213, 4413 | $2 \times \binom{n/4}{2}\binom{n/4}{1}^2$ | $\frac{6}{64} = 0.09375$ | $d_2(n_2)d_w(n_1)d_w(n_3)$ |
| 10 | 3312, 4412 | $2 \times \binom{n/4}{2}\binom{n/4}{1}^2$ | $\frac{6}{64} = 0.09375$ | $d_2(n_3)d_w(n_1)d_w(n_2)$ |
| 11 | 1113, 1114, 2223, 2224, 3331, 3332, 4441, 4442 | $4 \times \binom{n/4}{3}\binom{n/4}{1}$ | $\frac{4}{64} = 0.0625$ | $d_3(n_1)d_w(n_3 + n_4)$ |
| 12 | 2221, 2224, 3331, 3334, 4441, 4443 | $3 \times \binom{n/4}{3}\binom{n/4}{1}$ | $\frac{3}{64} = 0.046875$ | $d_3(n_2)d_w(n_1 + n_4)$ |
| 13 | 3331, 3332, 4441, 4442 | $3 \times \binom{n/4}{3}\binom{n/4}{1}$ | $\frac{3}{64} = 0.046875$ | $d_3(n_3)d_w(n_1 + n_2)$ |
| 14 | 1112, 1113, 4442, 4443 | $2 \times \binom{n/4}{3}\binom{n/4}{1}$ | $\frac{2}{64} = 0.03125$ | $d_3(n_3)d_w(n_2 + n_3)$ |
| 15 | 1111, 2222, 3333, 4444 | $4 \times \binom{n/4}{4}$ | $\frac{1}{64} = 0.015625$ | |

*FIG. 6A*

| N | Category 1 | Category 2 | Category 5 | Category 11 |
|---|---|---|---|---|
| 5 | 12341 | 11234 | 11342 | 11234 |
| 6 | 123412 | 112234 | 113422 | 112324 |
| 7 | 1234123 | 1122334 | 1134223 | 1123234 |
| 8 | 12341234 | 11223344 | 11342234 | 11232344 |
| 9 | 123412341 | 112213344 | 113412234 | 111322344 |
| 10 | 1234123412 | 1122123344 | 1134122342 | 1113222344 |

SWAP NETWORKS FOR QUANTUM COMPUTATION

BACKGROUND

An application of quantum computing is the evaluation (or simulation) of quantum systems. For example, it has been shown that quantum information and quantum computational methods may be employed to determine various properties of complex chemical compounds. Because the behavior of both a quantum-mechanical many-body system and an ensemble of interacting qubits within a quantum register are subject to the mechanics of quantum systems, various quantum-mechanical properties of materials (e.g., materials composed of chemical compounds) may be simulated via quantum computing. More succinctly, a system of N qubits may be employed to simulate the dynamics of quantum-mechanical many-body systems, where N scales linearly with the number of interacting particles.

Via conventional quantum computing methods, the circuit depth required to fully simulate chemical systems utilizing N qubits scales as $\mathcal{O}(N^5)$ or $\mathcal{O}(N^4)$, depending upon implementation details. Many interesting applications of quantum computational simulation, such as chemistry, include systems with a significantly large number of interacting particles. For example, large molecules may include tens or even hundreds of occupied orbitals. Even though, via conventional quantum computing methods, the scaling of the circuit-depth is polynomial, the circuit depth quickly becomes impractical for quantum computations requiring even modest values of N qubits.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

The various embodiments are directed towards quantum computers and methods of operating quantum computers to simulate the dynamics of many-body systems, such as but not limited to systems of non-local interactions of fermions (e.g., electrons). As a non-limiting example of an application, the embodiments may be employed to simulate (or compute) the time evolution of electronic orbitals in molecular chemistry, via quantum circuits (i.e., configurations of quantum logic gates) acting on the qubits of a register. More specifically, the embodiments include networks of swap gates that perform parallelized swap operations on the qubits or fermionic orbitals, which enable the simulation of non-local many-body interactions, via localized groupings of qubits within the quantum registers. Via the network of swap gates, the computation of the numerous many-body terms may be parallelized within the quantum computer, resulting in a significantly decreased circuit depth of the computer. The network of swap gates enables the iterative application of a small number of circuit templates, or even a single template, acting on the localized groupings of qubits to simulate the time-evolution of non-localized interacting quantum particles, such as but not limited to fermions.

One embodiment includes quantum hardware, computer or system configured to operate a network of quantum gates that operates on a set of qubits to perform a method. The quantum gates may include qubit swap gate. The set of qubits defines a plurality of 4-qubit combinations. For example, if the cardinality of the set is indicated by the positive integer N, the set of qubits may define $$\binom{N}{4}$$

unique 4-qubit combinations. The set may be an ordered set. The method may include iteratively updating the order of the set of qubits, via a plurality of qubit swap operations. The qubit swap operations may be implemented by the network of quantum gates. Via the iterative swap operations, each of the 4-qubit combinations is represented as a consecutive 4-qubit grouping within the order of the set of qubits, at least once during the plurality of swap operations. That is, each of the $$\binom{N}{4}$$

unique 4-qubit combinations is rendered as a consecutive 4-qubit grouping within the ordered set, at least once by the swap operations. Each pair of qubits swapped in each of the plurality of swap operations may be separated by at most three qubits within the order of the set of qubits.

In at least some of the embodiments, the set of qubits may further define a plurality of 2-qubit combinations. For instance, $$\binom{N}{2}$$

unique 2-qubit combinations may be defined by the set. The order of the set may be iteratively updated by additional qubit swap operations. Via the additional swap operations, each of the 2-qubit combinations is represented as a consecutive 2-qubit grouping within the order of the set of qubits, at least once during the additional swap operations. That is, each of the $$\binom{N}{2}$$

unique 2-qubit combinations is rendered as a nearest-neighbor 2-qubit pairing within the ordered set, at least once by the additional swap operations. Each pair of qubits swapped in each of the additional swap operations may be a nearest-neighbor pair or qubits within the order of the set of qubits.

BRIEF DESCRIPTION OF THE DRAWINGS

Aspects of the disclosure are described in detail below with reference to the attached drawing figures, wherein:

FIGS. 1A-1B provide schematic diagrams of quantum gates suitable for use in implementing embodiments of the present;

FIG. 1C shows one embodiment of a matrix representation of one embodiment of a 2-body time evolution operator that is consistent with the various embodiments;

FIGS. 2A-2E show five alternative embodiments for a 4-quibit quantum circuit implementing 4-quibit time evolution operator that is consistent with the various embodiments;

FIG. 4A provides a table that illustrates various properties for the class types of a 3-qubit interactions that are consistent with the various embodiments presented herein;

FIG. 4B provides a table that illustrates vectorizations of a configuration for 3-qubit combinations, where $5 \leq N \leq 10$ that are consistent with the various embodiments presented herein;

FIG. 4C provides a table that illustrates non-limiting embodiments of vectorizations for category 1 3-qubit combinations for N=14, 15, 16, 18, and 19;

FIG. 4D provides a table that illustrates other non-limiting embodiments of vectorizations for category 1 3-qubit combinations for N=14, 15, 16, 18, and 19;

FIG. 5B shows the swap operations of the process of FIG. 5A for an N=8 qubit quantum computer;

FIG. 6A provides a table that illustrates various properties for the class types of a 4-qubit interactions that are consistent with the various embodiments presented herein;

FIG. 6C provides a flow diagram that illustrates a process 620 of swap operations implemented by a 2-qubit slot network employed for 4-qubit embodiments discussed herein;

FIG. 7D shows the swap operations of the process of FIG. 7B for an N=10 qubit quantum computer;

DETAILED DESCRIPTION

Figure 2C:
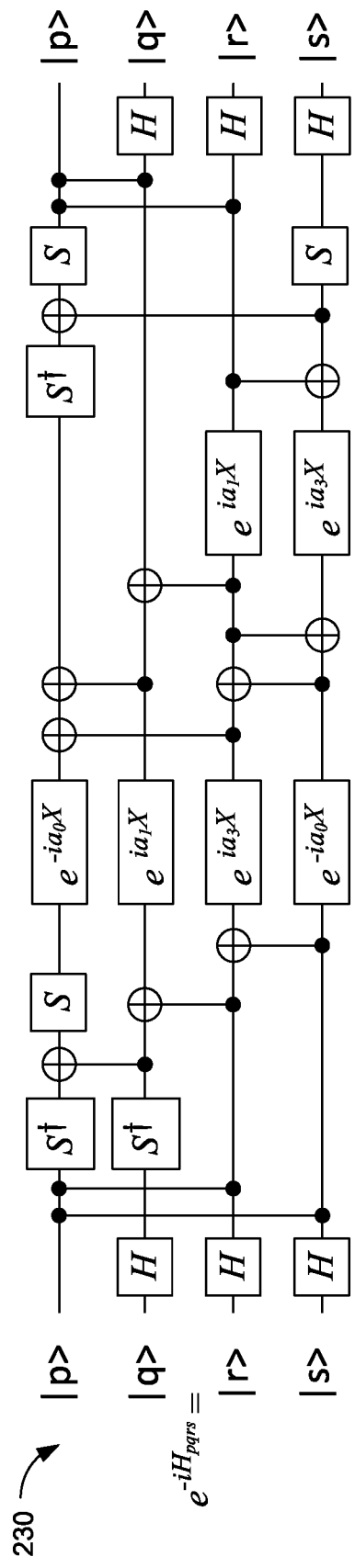
Figure 2D:
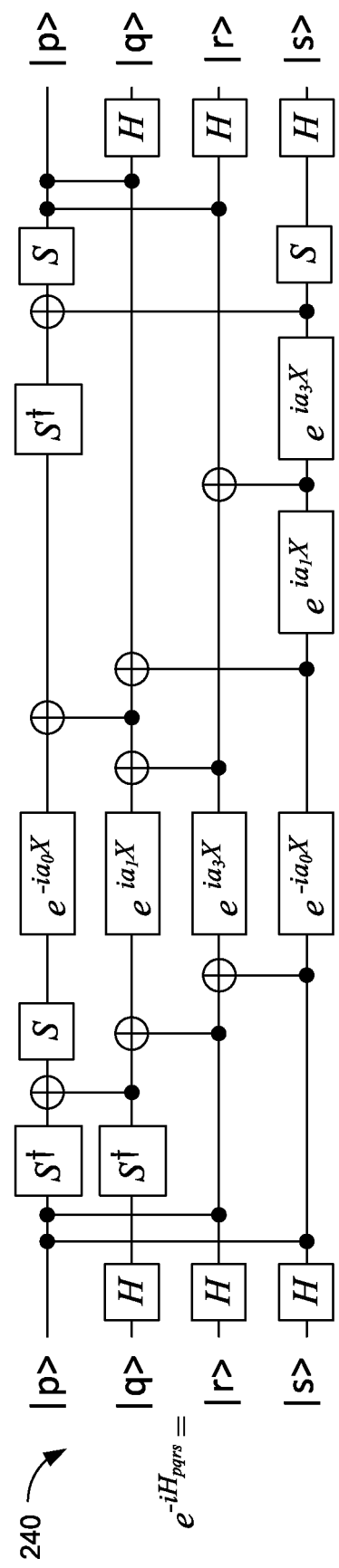
Figure 2E:
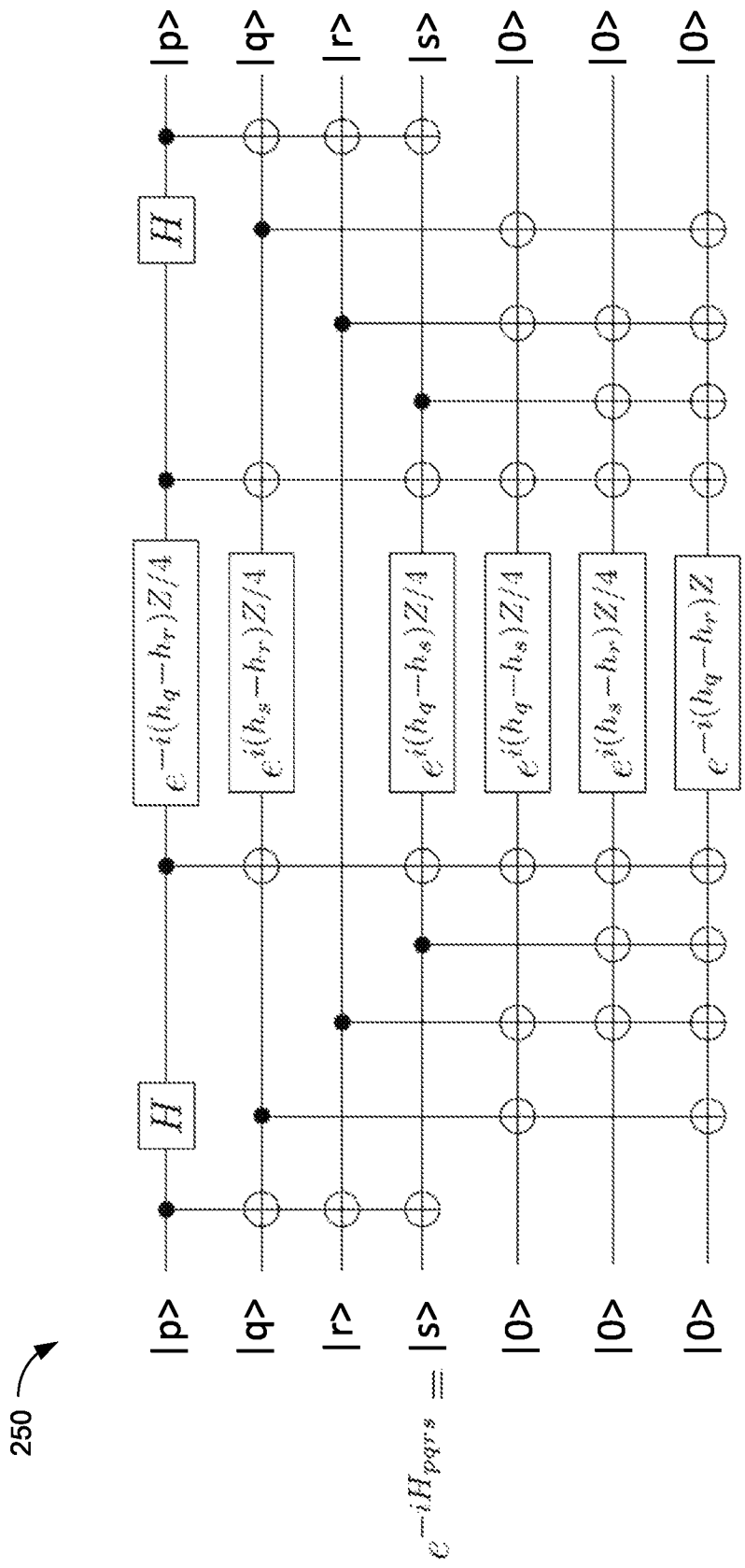

The subject matter of aspects of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. Each method described herein may comprise a quantum computing process, a classical computing process, and/or a combination thereof that may be performed using any combination of quantum and/or classical hardware, firmware, and/or software. For instance, various functions may be carried out by a processor executing instructions stored in memory. The methods may also be embodied as computer-usable instructions stored on computer storage media. The methods may be provided by a stand-alone application, a service or hosted service (stand-alone or in combination with another hosted service), or a plug-in to another product, to name a few.

As used herein, the term "set" may be employed to refer to an ordered (i.e., sequential) or an unordered (i.e., non-sequential) collection of objects (or elements), such as but not limited to qubits. A set may include N elements (e.g., qubits), where N is any non-negative integer. That is, a set may include 0, 1, 2, 3, . . . N objects and/or elements, where N is an positive integer with no upper bound. Therefore, as used herein, a set may be a null set (i.e., an empty set), that includes no elements. A set may include only a single element. In other embodiments, a set may include a number of elements that is significantly greater than one, two, or three elements. As used herein, the term "subset," is a set that is included in another set. A subset may be, but is not required to be, a proper or strict subset of the other set that the subset is included in. That is, if set B is a subset of set A, then in some embodiments, set B is a proper or strict subset of set A. In other embodiments, set B is a subset of set A, but not a proper or a strict subset of set A.

The various embodiments are directed towards quantum computers and methods of operating quantum computers to simulate the dynamics of many-body systems, such as but not limited to systems of non-local interactions of fermions (e.g., electrons). As a non-limiting example of an application, the embodiments may be employed to simulate (or compute) the time evolution of electronic orbitals in molecular chemistry, via a quantum circuits (i.e., configurations of quantum logic gates) acting on the qubits of a register. More specifically, the embodiments include networks of swap gates that perform parallelized swap operations, which enable the simulation of non-local many-body interactions. In some embodiments, the swap operations include qubit swap operations that localize groupings of qubits within the quantum registers. In other embodiments, the swap operations are employed to swap fermionic orbitals. That is, swap operations that include fermionic swap operations may swap Hamiltonian terms to enable localized groupings of terms in the Hamiltonian.

Under the second quantization form, a mapping between a Hamiltonian function corresponding to the many-body interactions of electronic orbitals and a Hamiltonian function corresponding to the many-body interactions of the qubits of a quantum computer, may be generated via the canonical creation and annihilation operators. Because of this mapping of the Hamiltonian functions, quantum circuits, which are designed to emulate the properties of the time-evolution operator of various terms of the orbitals' Hamiltonian, may operate on the qubits. The orbitals' second quantization Hamiltonian includes both one-body and two-body terms. The Hamiltonian is non-local and the one-body terms correspond to the 2-qubit interactions between the qubits of each possible pairing of two qubits within the quantum register. Thus, to evaluate all of the one-body terms, a circuit corresponding to the one-body time-evolution operator must operate on each possible pairing of qubits. The two-body terms correspond to 4-qubit interactions between each possible grouping of four qubits within the register. To evaluate all of the two-body terms, a circuit corresponding to the two-body time-evolution operator must operate on each possible grouping of four qubits.

The combinatorics of the 4-qubit configurations scale significantly faster than the combinatorics of the 2-qubit terms, and thus the 4-qubit terms dominate the circuit depth for such a computational scheme. Via conventional quantum computing methods, the circuit depth required to fully simulate chemical systems utilizing N qubits scales as $\mathcal{O}(N^4)$. Many interesting applications of quantum computational simulation, such as chemistry, include systems with a significantly large number of interacting particles. For example, large molecules may include tens or even hundreds of occupied orbitals. Even though, via conventional quantum computing methods, the scaling of the circuit-depth is polynomial, the circuit depth quickly becomes impractical for quantum computations requiring even modest values of N qubits. As discussed below, the circuit depth of at least some of the various enhanced embodiments herein scales as approximately $\mathcal{O}(N^3)$, providing at least an order of magnitude reduction in the circuit depth. Thus, the various embodiments clearly provide a significant improvement to the performance, functionality, and efficiency of quantum computer and the methods of operating quantum computers.

As noted above, the embodiments include qubit-swap networks, comprising of a plurality of swap gates. Although many of the embodiments discussed here are directed towards swap networks that swap the qubits of a quantum register, other embodiments are not so limited. The swap operations may readily be employed as fermionic swap operations via fermionic swap operations. It is understood that any of the swap operations that are discussed herein as qubit swap operations may be readily generalized to include fermionic swap operations. That is, any of the swap networks and/or swap gates discussed herein may act as fermionic swap operators that swap fermionic orbitals and/or the Hamiltonian terms that represent fermionic orbitals. Similar to the qubit swap operations, the fermionic swap operations may be parallelized swap operations.

The qubit and/or fermionic orbital swap operations enable the simulation of non-local many-body interactions, via localized groupings of qubits within the quantum registers and/or localized groupings of fermionic orbitals. Via the network of swap gates, the computation of the numerous many-body terms may be parallelized within the quantum computer, resulting in a significantly decreased circuit depth of the computer. The network of swap gates enables the iterative application of a small number of circuit templates, or even a single template, acting on the localized groupings of qubits to simulate the time-evolution of non-localized interacting quantum particles, such as but not limited to fermions. In conventional methods of architecting a quantum computer for such simulation schemes, circuit depth of the computer is dominated by the 2-body Hamiltonian terms, which correspond to the 4-qubit interactions, and scales as $\mathcal{O}(N^4)$. As shown in FIG. 7E, via the circuit parallelization enabled by the swap networks, the circuit depth of the enhanced embodiments herein scales as $\mathcal{O}(N^3)$. Thus, the various embodiments provide at least an order of magnitude reduction in the scaling of the depth of the circuits required from simulation.

Many of the various embodiments discussed herein are directed towards simulating Hamiltonian terms corresponding to non-local 1-body and 2-body fermionic interactions. That is, when simulating the effects of the Hamiltonian, higher-order terms are neglected. However, the embodiments are not so limited, and the embodiments may be generalized to include higher order terms by including k-body interactions, where k is any integer greater than 1. For example, to compute the 3-body Hamiltonian terms, the swap networks (and other circuits), as well as the various methods, processes, and computational systems discussed herein may be scaled up to incorporate 8-qubit (or any other higher-order) interactions in the quantum circuits. Such embodiments may include appropriately scaled swap networks to localize all possible 8-qubit groupings. The embodiments may also be generalized to simulate a similar Hamiltonian for bosons. The disclosed methods and systems may be applied to systems based on a variety of physical implementations and/or instantiations of qubits such as those based on trapped ions, cold atoms, Josephson junction devices, solid state spin, Majorana fermions, photon polarization, among others. In some applications, so-called topologically protected qubits are preferred to provide fault tolerance.

As discussed herein, a quantum computer, or one or more quantum registers within the computer, may include one or more sets of qubits. At least one of the one or more sets included in a computer includes N qubits, where N is any positive integer greater than 1. In various embodiments, a set of qubits may be an ordered set of qubits. In some of the embodiments the order of the set may be a logical and/or virtualized order. The logical and/or virtualized order of the qubits may or may not be similar to any physical ordering, configuring, and/or arranging of the physical instantiations of the qubits. When discussing the order of any set of qubits, unless stated otherwise, it is the logical and/or virtualized ordering of the qubits, which may be separate from any physical ordering of the physical instantiations of the qubits. Accordingly, the terms "logical" or "virtual" may be omitted when discussing the order of the set, because unless otherwise, it is implied that it is the logical and/or virtualized order of the set that is being discussed.

The various embodiments may iteratively update the order of the set, via qubit swap operations, such that a current order of the set may be updated numerous times during the methods and/or processes discussed herein. A logical and/or virtualized configuration and/or arrangement of the qubits may indicate a current logical and/or virtual order of the set, and may reference and/or indicate each qubit, via a unique integer index between 1 and N. Thus, when discussing the logical and/or virtualized arrangement and/or configuration of qubits, the logical and/or virtualized arrangement and/or configuration may be discussed in the context of a 1D array, string, and/or lattice of qubits. For example, a logical and/or virtualized arrangement and/or configuration of N=10 qubits may be represented as a logical or virtual 1D array: (1,2,3,4,5,6,7,8,9,10).

However, the physical instantiation of the set of qubits may include a physical arrangement and/or physical configuration of the qubits that is not a 1D lattice or string of physical qubits. In some embodiments, the physical instantiations of the qubits may be physically arranged and/or configured in a 2D or 3D physical array, string, or lattice. In other embodiments, the physical instantiations of the qubits may be physically arranged and/or configured in a 1D physical array, string, or lattice. Thus, when discussing the embodiments, the logical and/or virtualized arrangement and/or configuration of the qubits, which is a 1D array, may be different than the physical arrangement and/or configuration (which may include more than one dimension). Thus, when discussing any arrangement, configuration, and/or ordering of the qubits, unless noted otherwise, the logical and/or virtualized arrangement or configuration is implied. That is, unless stated otherwise, when discussing the arrangement, configuration, and/or ordering of the qubits, it is implied that the logical and/or virtualized arrangement, and not the physical arrangement, that is being referenced. Accordingly, in the discussion below, the terms logical and/or virtualized may be omitted, because it is implied that it is the logical and/or virtualized arrangements and/or ordering that are being discussed.

The order of the set is indicated by the qubits' logical or virtual position within the logical or virtual 1D array. Thus, in the N=10 example above, qubit 1 (which may be indicated via bra and ket notation: $\langle 1|$ or $|1\rangle$, respectively) is in the $1^{st}$ logical position of the array, qubit 2 is in the $2^{nd}$ logical position of the array, and qubit 10 is in the tenth logical position of the array. As noted above, the logical order of the sets may be updated, resulting in updating of the logical arrangement and/or logical configuration of the qubits.

As discussed throughout, the re-ordering of the set may be enabled via one or more qubit swap operations. A qubit swap operation, operating on a pair of qubits, may "swap" the logical positions of the two qubits in the pair. Swapping the logical positions of the qubits may re-order or update a current ordering of the set. For example, a swap operation, operating on qubits 1 and 2, may logically re-order the set of qubits, such that the logical arrangement and/or logical configuration is updated to: (2,1,3,4,5,6,7,8,9,10), where qubit 2 is in the logical $1^{st}$ position and qubit 1 is in the logical $2^{nd}$ position of the set. In various embodiments, swap operations may be parallelized across ordered set of qubits, such that a parallelized swap operation may simultaneously (or near simultaneously) may reorder the previous array: (1,2,3,4,5,6,7,8,9,10)→(2,1,4,3,6,5,8,7,10,9), where the swap operations swapped the qubits located in the logical positions: {1,2}, {3,4}, {5,6}, {7,8}, and {9,10}. Such a swap operation may be indicated in matrix notation as:

$$\begin{pmatrix} 1,2,3,4,5,6,7,8,9,10 \\ 2,1,4,3,6,5,8,7,10,9 \end{pmatrix},$$

where the top row indicates the initial ordering of the set and the next row indicates the updated order that resulted from the parallelized swap operation.

In the various embodiments, networks of qubits swap gates (i.e., swap networks) are employed to swap the logical positions of two qubits logically located at specific logical positions within the set. Such qubit swap gates are discussed in conjunction with at least FIG. 1B. It should be noted that swapping the logical positions of qubits, via swap operations, may conserve the physical arrangement and/or physical ordering of the physical instantiations of the qubits. More specifically, a qubit swap operation may swap the quantum states of the two affected qubits and not affect any physically observable configuration of the physical instantiation of the qubit. In the above swap operation on qubits 1 and 2, the qubit initially in the $1^{st}$ logical position of the array may be in the quantum state (i.e., a superposition of the two eigenstates of the qubits) represented as: $|1\rangle = \alpha|\uparrow\rangle + \beta|\downarrow\rangle$. The qubit in the $2^{nd}$ logical position of the array may be in a second quantum state represented as: $|2\rangle = \alpha'|\uparrow\rangle + \beta'|\downarrow\rangle$. $(|\uparrow\rangle, |\downarrow\rangle)$ comprise an orthogonal basis for the qubits, $\alpha$, $\beta$, $\alpha'$, and $\beta'$ are complex amplitudes (or coefficients), and $|\alpha|^2 + |\beta|^2 = |\alpha'|^2 + |\beta'|^2 = \langle\uparrow|\uparrow\rangle = \langle\downarrow|\downarrow\rangle = 1$ and $\langle\uparrow|\downarrow\rangle = \langle\downarrow|\uparrow\rangle = 0$. After the swap operation operates on the qubits in the $1^{st}$ and $2^{nd}$ positions of the array, the qubit in the first position is in the quantum state: $|2\rangle = \alpha'|\uparrow\rangle + \beta'|\downarrow\rangle$, and the qubit in the $2^{nd}$ position in the array is in the quantum state: $|1\rangle = \alpha|\uparrow\rangle + \beta|\downarrow\rangle$. Thus, it may be said that the ordering and/or positions of qubits 1 and 2 have been logically swapped. Note that any physical ordering or configuration of the physical instantiations (e.g., individual electrons) need not be swapped for the quantum states of the qubits to be logically swapped.

The Physics of Molecular Chemistry Dynamics

The disclosed methods and systems generally pertain to quantum computation based on a second-quantized Hamiltonian associated with a material of interest. The second-quantized Hamiltonian can be mapped to qubits, and logical states of each qubit can be associated with occupancy of a single-electron spin-orbital, wherein 0 denotes occupied, and 1 denotes unoccupied. A system with a plurality of single-electron spin-orbitals may be represented, within a quantum computer, by N qubits. Systems with any numbers of electrons can be represented by appropriately scaling the value of N. In the following discussion, N may be any integer greater than 1. That is, N is not associated with an upper bound. In some embodiments, N is greater than 50. In some embodiments, N is significantly greater than 100, or even 1000.

The Jordan Wigner transformation may be used to transform creation and annihilation operators so as to be represented using Pauli spin matrices. While a general time-evolution operator for a multi-body system may not be readily representable as a sequence of gates, the second quantized Hamiltonian may be expressed as a sum of one and two-electron terms. The time-evolution operators of each of the terms may be physically implemented via a sequence of quantum logic gates. The associated unitary time evolution operator may be approximated using Trotter-Suzuki relations based on time-evolution of non-commuting operators Quantum computations for multi-body systems may be formulated in the second quantization form, wherein the Hamiltonian operator is expressed as:

$$H = \Sigma_{p,q} h_{pq} a_p^\dagger a_p + \Sigma_{p,q,r,s} h_{pqrs} a_p^\dagger a_q^\dagger a_r a_s,$$

and wherein p, q, r, and s are indexes identifying molecular orbitals, with each molecular orbital occupied by either a spin-up or spin-down particle, or both or neither. The $h_{pq}$ and $h_{pqrs}$ coefficients are amplitudes associated with the various wave functions. The $a^\dagger$ and a operators, respectively, are the canonical particle creation and annihilation operators of the second quantized form of quantum mechanics. The higher order terms are neglected in this formulation. However, it should be noted that these terms may be included in the various embodiments, by employing swap networks that are directed towards k-body interactions, where k is greater than 4.

The $h_{pq}$ and $h_{pqrs}$ coefficients may be exactly determined or approximated. For example, these coefficients may be approximated by carrying out the appropriate integration of the Hartree-Fock method. For convenient description, the $h_{pq}$ and $h_{pqrs}$ coefficients are referred to herein as 1-body Hamiltonian coefficients and 2-body Hamiltonian coefficients, respectively. These coefficients are complex coefficients for wave functions that couple basis states p and q and p, q, r, and s, respectively, wherein p, q, r, and s, are integer indexes. These 1-body and 2-body Hamiltonian coefficients can be obtained in a variety of different ways using, for example, conventional computer programs that carry out computations, such the spatial integrations under the Hartree-Fock approximation. Coefficients obtained in any manner can be used in the examples below. It should be noted that the creation and annihilation operators may be expressed via the Hermitian and unitary 2×2 Pauli-spin matrices, herein referenced as X, Y, and Z.

For purposes of quantum computation, each orbital is mapped to two qubits, where the $h_{pq}a_p^\dagger a_q$ terms operate on pairs of qubits, indexed as p and q (representing one electron) and the $h_{pqrs}a_p^\dagger a_q^\dagger a_r a_s$ terms operate on groupings of four qubits, indexed as p, q, r, and s (representing two electron).

The time evolution of the orbitals is generated via a unitary time-evolution operator $U(t)=e^{-iHt}$ acting on the orbitals' wavefunctions. Thus, given an initial wavefunction ($\psi(t=0)$) for the orbitals, the time evolution of the orbitals may be determined as: $\psi(t)=e^{-iHt}\psi(0)$. Note that in general, Hamiltonian's terms do not commute. However, evaluation of the U(t) may be approximated via discrete evaluations iterated over time (e.g., Trotter steps) as:

$$U(t) \approx \left(\prod_j e^{\frac{-iH_j \Delta t}{M}}\right)^M,$$

where M is the number of Trotter steps, $\Delta t$ is the Trotter step size, and $H_j$ are the terms of the Hamiltonian. Thus, the time-evolution operator may be approximated at each Trotter step as:

$$U(t) \approx \prod_{p,q} e^{-iH_{pq}t} \prod_{p,q,r,s} e^{-iH_{pqrs}t},$$

where $H_{pq}=h_{pq}a_p^\dagger a_p$ and $H_{pqrs}=h_{pqrs}a_p^\dagger a_q^\dagger a_r a_s$. Thus, the time evolution of such orbitals may be simulated, via a quantum computing system that includes gates that operate on the qubits, via the exponentiated operations of the Hamiltonian.

Note that the Hamiltonian includes all non-local interactions for the electrons. Thus, when mapped to N qubits there are $$\binom{N}{2}$$

1-body time evolution operations and $$\binom{N}{4}$$

2-body time evolution operations required for each pairing and grouping of four qubits. A quantum circuit is required for each such operation, where each circuit includes one or more quantum gates. Because the 1-body Hamiltonian terms scale as $O(N^2)$ and the two-body Hamiltonian terms scale as $O(N^4)$, the 2-body terms dominate the circuit depth required for the quantum computation. Thus, the following discussion regarding the quantum circuits and gates for computing the terms will be directed towards the two-body terms. However, other quantum circuits and gates may be included for the computation of the 1-body terms.

As noted above, in general the terms of the Hamiltonian do not commute. Thus naively, $h_{pqrs}a_p^\dagger a_q^\dagger a_r a_s$ implicitly includes the summation of 4!=24 permuted terms. However, by requiring the coefficient to be real-valued and employing 8-fold rotational symmetry in the Hartree-Frock integrals, there are only three unique terms: $h_q = h_{pqrs}\delta_{o_q o_r}\delta_{o_p o_s}$, $h_s = h_{psqr}\delta_{o_s o_q}\delta_{o_p o_r}$, and $h_r = h_{prsq}\delta_{o_r o_s}\delta_{o_p o_q}$. The Kronecker delta functions are applied to the spin-states of the orbitals, and result from the integration of the inner products of the two orbitals' spin wavefunctions. Thus, when mapped to qubits, for the terms to be non-zero, the states of the two inner qubits must be equivalent and the states of the outer two qubits must be equivalent. When expressed in a matrix form, this property increases the sparsity of the matrix. For clarity in the following discussion, the Delta direct functions will omitted, but will be understood to be included.

By expressing the creation and annihilation operators as Pauli-spin matrices, via the Jordan-Wigner transformation, it can be shown that:

$$\sum h_{pqrs}a_p^\dagger a_q^\dagger a_r a_s = H_{pqrs} = \frac{(h_q - h_r)}{2}(X_p X_q X_r X_s + Y_p Y_q Y_r Y_s) + \frac{(h_s - h_r)}{2}(X_p X_q Y_r Y_s + Y_p Y_q X_r X_s) + \frac{(h_q - h_s)}{2}(X_p Y_q Y_r X_s + Y_p X_q X_r Y_s),$$

where $X_i$, $Y_i$, and $Z_i$ are the Pauli-spin matrices acting on the corresponding qubit. The summation on the left-hand side of the above equality is over the spin-states of the orbitals (or states of the corresponding qubits). As noted above, the symmetry requirement of the states of the inner two qubits and the symmetry requirement of the states of the outer two qubits is implied, which as shown on the right-hand side of the above equality, significantly reduces the number of non-zero terms. Each of these three terms on the right represents two rotational operations on each of the four qubits. Thus, the computation of each two-body term requires six rotational operations on the four corresponding qubits.

Each qubit is a superposition of two states, and $\Sigma h_{pqrs}a_p^\dagger a_q^\dagger a_r a_s$ operates on the generally entangled 4-qubit combination: $|p\rangle \otimes |q\rangle \otimes |r\rangle \otimes |s\rangle$. Thus, $e^{-iH_{pqrs}t}$ is represented as a 16×16 rotational matrix, where the exponentiation is applied to the matrix elements. Likewise, $e^{-iH_{pq}t}$ is represented as a 4×4 rotational matrix. FIG. 1C shows one embodiment of a matrix representation 140 of one embodiment of a 2-body time evolution operator (i.e., $e^{-iH_{pqrs}t}$) that is consistent with the various embodiments. As shown in exponentiated matrix 140 of FIG. 1C, many (but not all) of the off-diagonal terms of the $e^{-iH_{pqrst}}$ matrix are identically 0 due to the symmetry requirements on the spin-states of the orbitals. Note that the t factor in each of the matrix elements is implied, but not explicitly shown.

Various enhanced quantum circuits and quantum circuits for simulating the time evolution of the orbitals' wavefunctions associated with the Hamiltonian's two-body terms, are discussed in conjunction with at least FIGS. 1A-1B and FIGS. 2A-2E. Each of the quantum circuits shown in FIGS. 2A-2D distribute the 6 rotations among the four interacting qubits, without requiring ancilla qubits. These embodiments are not so constrained, and other embodiments may include circuits that do employ ancilla qubits. One non-limiting example of a circuit that employs ancilla qubits is provided by FIG. 2E.

Note that the 2-body terms are maximally non-local, and a circuit performing the rotations must act on each of the $$\binom{N}{4}$$

groupings of the qubits. The circuit depth of conventional methods for designing quantum circuits to act on every 4-tuple of qubits scales as $O(N^5)$. However, in the various enhanced embodiments herein, a network of qubit swap gates is employed to render each of the non-local interactions to be local. That is, via the various swap networks discussed herein, a quantum circuit for calculating the two-body terms may act only on groupings of four-nearest neighboring qubits. Accordingly, a circuit template (e.g., one or more of the embodiments of FIGS. 1A-1D) may be iteratively employed on groupings of four-nearest neighboring qubits. Furthermore, the swap operations and the circuit template may be parallelized, which as shown in the numerical results of FIG. 7D, drastically reduces the scaling of the circuit depth to approximately $O(N^3)$.

Embodiments of Quantum Gates and Quantum Circuits

FIGS. 1A-1B provide schematic diagrams of quantum gates suitable for use in implementing embodiments of the present disclosure. More specifically, FIG. 1A provides various circuit schematic symbols for single-qubits gates that are employed in the various embodiments. FIG. 1B provides schematic symbols for multi-qubit gates. FIG. 1A shows X gate 102, Y gate 104, Z gate 106, H gate 108, S gate 110, $S^\dagger$ gate 112 (i.e., S conjugate transpose or S dagger gate), T gate 114, and exponential gate 116. Each of these gates act to rotate a single qubit (e.g., rotations around a Bloch sphere). X gate 102, Y gate 104, and Z gate 106 may be referred to, either collectively or individually, as Pauli-spin gates and/or matrices. H gate 108 may be referred to as a Hadamard gate or a square root of NOT gate. Via qubit rotations, each of gates 102-116 introduces a relative phase difference to the state of the qubit. The 2×2 matrix form of each of gates 102-116, written in the standard basis, is as follows:

$$X \text{ gate } 102 = \begin{bmatrix} 0 & 1 \\ 1 & 0 \end{bmatrix}, Y \text{ gate } 104 = \begin{bmatrix} 0 & -i \\ i & 0 \end{bmatrix},$$

$$Z \text{ gate } 106 = \begin{bmatrix} 1 & 0 \\ 0 & -1 \end{bmatrix}, H \text{ gate } 108 = 1/\sqrt{2}\begin{bmatrix} 0 & 1 \\ 1 & 0 \end{bmatrix},$$

-continued $$S \text{ gate } 110 = \begin{bmatrix} 1 & 0 \\ 0 & i \end{bmatrix}, S^\dagger \text{ gate } 102 = \begin{bmatrix} 1 & 0 \\ 0 & -i \end{bmatrix},$$

$$T \text{ gate } 114 = \begin{bmatrix} 1 & 0 \\ 0 & e^{i\pi/4} \end{bmatrix},$$

and exponential gate $$116 = \sum_{k=0}^{\infty} \frac{(-i)^k}{k!} A^k,$$

where A is a 2×2 matrix.

FIG. 1B shows multi-bit quantum gates: C-NOT gate 120 and four swap gates 130, 132, 134, and 136. C-NOT 120 gate (controlled-NOT gate) and swap gate 130 act on two qubits, labeled via ket notation $|1\rangle$ and $|2\rangle$. Swap gates 132, 134, and 136 act on three, four, and five bits respectively, where the additional qubits are labelled as $|3\rangle$, $|4\rangle$, and $|5\rangle$, respectively. The labeling on the inputs and outputs on the qubits lines explicitly represents the swapping of the quantum states of the qubits. The multiple qubits may or may not be entangled. The 4×4 matrix forms of C-NOT gate 120 and 2-qubit swap gate 130, written in the standard basis, are as follows:

$$C-NOT \text{ gate } 120 = \begin{bmatrix} 1 & 0 & 0 & 0 \\ 0 & 1 & 0 & 0 \\ 0 & 0 & 0 & 1 \\ 0 & 0 & 1 & 0 \end{bmatrix} \text{ and}$$

$$\text{swap gate } 130 = \begin{bmatrix} 1 & 0 & 0 & 0 \\ 0 & 0 & 1 & 0 \\ 0 & 1 & 0 & 0 \\ 0 & 0 & 0 & 1 \end{bmatrix}.$$

For brevity, the 8×8, 16×16, and 32×32 matrices of swap gates 132, 134, and 136, are omitted. However, these matrices may be similarly generated. In qubit-swap notation used throughout, swap gate 130 may be employed to swap nearest neighbor qubits $(1,2) \rightarrow (2,1)$. Employing multiple instantiations of nearest neighbor swap gate 130, non-neighboring qubits may be swapped. More specifically, any pair of qubits, where the degree of locality is indicated by positive integer k, may be swapped by employing multiple instances of nearest-neighbor swap gate 130 (where k=1, indicated a nearest-neighbor qubit swap). For swap gate 132: k=2, for swap gate 134: k=3, and for swap gate 136: k=4. In the qubit-swap notation used throughout, swap gate 132 swaps qubits: $(1,2,3) \rightarrow (3, 2,1)$, swap gate 134 swaps qubits: $(1,2,3,4) \rightarrow (4,2,3,1)$, swap gate 136 swaps qubits: $(1,2,3,4,5) \rightarrow (5,2,3,4,1)$. For each of the embodiments of fermionic swap networks discussed herein: $1 \leq k \leq 4$, however swap gates 132-136 demonstrate how any pair of qubits may be swapped employing only multiple instances of nearest-neighbor swap gate 130. That is, k has no upper limit for the various embodiments.

Various combinations of any of the quantum gates shown in FIGS. 1A-1B may be employed to construct the quantum circuits utilized in the various embodiments. Additional quantum gates, such as but not limited controlled-Z gates, controlled phase gates, Toffoli gates, Fredkin gates, measurement gates, and the like, may be combined with the gates of FIGS. 1A-1B in the various embodiments.

As noted above, to fully simulate quantum chemistry, the 1-body time evolution operator $e^{-iH_{pq}t}$ must operate on each $$\binom{N}{2}$$

pairing of qubits and the 2-body time evolution operator $e^{-iH_{pqrs}t}$ must operate on each of the $$\binom{N}{4}$$

groupings of 4 qubits. When discussing application to qubits, the 1-body time evolution operator $e^{-iH_{pq}t}$ may be referred to as a 2-qubit operator. Similarly, the 2-body time evolution operator $e^{-iH_{pqrs}t}$ may be referred to as a 4-qubit operator. Each of these 2-quibit and 4-qubit operators correspond to a 2-quibit quantum circuit and a 4-qubit quantum circuit, respectively. These quantum circuit may be comprised of various combinations of the quantum gates discussed in conjunction with FIGS. 1A-1B. As noted above, FIG. 1C shows one embodiment of a matrix representation 140 of the 2-body time evolution operator $e^{-iH_{pqrs}t}$, where the t factor in each of the matrix element is implied.

FIGS. 2A-2E show five alternative embodiments for a 4-quibit quantum circuit corresponding to the 4-qubit time evolution operator $e^{-iH_{pqrs}t}$. Although not shown, similar two-qubit quantum circuits may be employed for the 2-quibit time evolution operator $e^{-iH_{pq}t}$. Because the implementation of the 4-qubit operators dominate the circuit depth of the computation, the following discussion will focus on the implementation of the 4-qubit operators.

Each of the four circuits of FIGS. 2A-2E: 210, 220, 230, 240, and 250 respectively, include a four qubit input and four qubit output, where the four qubits are represented as: |p⟩, |q⟩, |r⟩ and |s⟩. Each of circuits 210, 220, 230, and 240 perform the 6 rotations of the of 2-body time evolution operator, distributed over the four qubits, via an exponential operator (e.g., exponential operator 116 of FIG. 1A). However, the circuits 210, 220, 230, and 240 vary on the rotation depth (i.e., the maximum number of rotation performed on a single qubit). The circuits also vary in the number of two-qubits gates (e.g., C-NOT gate 120 of FIG. 1B) required for implementation. Various implementation tradeoffs may be achieved by varying the rotational depth and number of 2-quibit gates in the embodiments. More specifically, quantum circuit 210 of FIG. 2A balances the 6 rotations amongst the 4 qubits (i.e., two rotations for each of qubits: |p⟩, |q⟩, and |s⟩, and no rotations for qubit |r⟩. The rotation depth of a circuit may be the maximal number of rotations for any qubit in the circuit. Thus, circuit 210 has a rotation depth of 2), and utilizes 18 2-qubit gates. Quantum circuit 220 of FIG. 2B has a rotation depth of 2 and utilizes 16 2-qubit gates. Quantum circuit 230 of FIG. 2C has a rotation depth of 2 and utilizes 14 2-qubit gates. Quantum circuit 240 of FIG. 2D has a rotation depth of 3 and utilizes 12 2-qubit gates. Quantum circuit 250 of FIG. 2E employs three ancilla qubits. Via various manipulations, it can be shown that quantum circuit 250 may be transformed and/or reduced into any of quantum circuits 200, 210, 230, or 240.

Embodiments of Fermionic Swap Networks

As noted above, to simulate quantum chemistry, as well as other many-body quantum systems, the multiple quantum bodies are mapped to N qubits, where N is an unbounded integer greater than 1. The embodiments discussed herein will consider 1-body and 2-body local and non-local terms of the second quantized Hamiltonian. Note, the 1-body terms (of the 1-body time evolution operator $e^{-iH_{pq}t}$) may be simulated via a 2-qubit operator operating on each $$\binom{N}{2}$$

pairing of qubits and the 2-body terms (for the 2-body time evolution operator $e^{-iH_{pqrs}t}$) may be simulated via a 4-qubit operator operating on each of the $$\binom{N}{4}$$

groupings of 4 qubits. FIGS. 2A-2E show various embodiments of quantum circuits for implementing these 4-qubit operators.

A "quantum register" or simply a "register" may include or represent a set of N qubits, where N is any integer greater than 1. N may be referred to as the depth of the register. As noted above, the set may include a logical order and the set may be logically configured as a logical 1D array, where each of the N qubits is associated with a logical position or location within the array. Because the logical positions of qubits are iteratively swapped, the order (or sequence) of the qubits is varied during the methods and processes discussed herein. For the following discussion, the qubits are logically arranged in a 1D array. However, other embodiments are not so constrained, and the methods and operations discussed may be generalized into 2D and 3D arrays of qubits. An ordered string of qubits may be referenced notation: (1, 2, 3, 4, . . . N−3, N−2, N−1, N), where the integers refer to a unique index for each qubit. In addition to an index, each qubit has a logical position within the register. The current position of a qubit in a register is dependent upon the current order of the string of qubits. As discussed throughout, swap operations are iteratively performed on the qubits, such that a qubit's position in the register (and thus the order of the qubits) is iteratively updated, but its unique index is constant. In the above 1D array, the qubit indexed as 1 is in the $1^{st}$ position and the qubit indexed as 2 is in the $2^{nd}$ position. If qubits 1 and 2 are swapped, the updated order of the register would be notated as: (2, 1, 3, 4, . . . N−3, N−2, N−1, N), where the integers refer to the index of the qubits. Qubit 2 is now in position 1 and qubit 1 is now in position 2.

"Nearest neighbor" qubits are two logically-consecutive qubits in the register. Thus, two nearest-neighboring pairs of qubits in both the above register arrangements include the two-qubits pairings of: (1,2) and (N−1, N−2). For a positive integer k, such that 2≤k≤N, a local grouping of k-qubits includes a combination of k logically consecutive (within the register) qubits. Thus a local grouping of four qubits, in the initial register arrangement, include the four-qubit groupings of (1,2,3,4) and (N−3, N−2, N−1, N).

A "qubit wheel" or simply a "wheel" may be a logically ordered grouping of qubits within a quantum register. Thus, a wheel may be a logical construct, rather than a physically grouping of qubits. As described below, a wheel may include a subset of a set of qubits within the register. In some embodiments, a wheel includes a subset of the N qubits within the register. The cardinality of the ordered subset of qubits included in a wheel may be indicated as n, where 1≤n≤N. n may be referred to as the depth of the wheel. For some wheels, the qubits of the wheel may be logically consecutive qubits in the 1D array representing the logical order of the register. For other wheels, the qubits of the wheel may be separated by one or more qubits within the array of the register. That is, via the ordering of the register, a wheel may not be a local grouping of qubits. Similar to a register, the qubits within a wheel are ordered. Accordingly, a qubit included in a wheel may have a position in the wheel, as well as a position within the register. A qubit may have a first position that is the qubit's position within a register, and a second position that is the qubit's position within a wheel. Because the qubits are iteratively swapped, the qubit's position within the wheel (and thus the order of the wheel) may be iteratively updated. Note that two qubits included in the same wheel may be nearest-neighboring qubits within the wheel, but not nearest neighbor qubits within the register. Two qubits may be nearest-neighboring qubits within a register, but are not included in the same wheel. As discussed below, in some embodiments, the register's ordered set of qubits is subdivided into k ordered wheels of approximately equal depth or cardinality. Each of the k wheels includes a subset of the set of qubits. Each of the subsets of qubits may be disjoint from all the other subsets of qubits. That is, each qubit of the register may be assigned to exactly 1 of k wheels.

Qubits within a register and/or a wheel may be swapped. A swap operation of qubits may be referred to as a rotation of the register (or wheel). The notation $\{i,j\}$, where $1 \leq i \neq j \leq N$ is adopted to refer to a qubit swap operation that swaps the qubits in the ith and jth logical positions within the register (or wheel). That is, the notation $\{i,j\}$ may reference positions within a wheel or register, depending upon the context. In some embodiments, portions of the iterative qubit swaps are parallelized. That is, multiple pairs of qubits may be swapped in the same swapping (or rotation) operation. Parallelized qubit swap may be notated as: $\{\{i,j\}, \{j,k\}\}$, where the double $\{\{\ \}\}$ indicates multiple (or parallelized) swaps in the same swap or rotation operation. In some embodiments, alternating pairs of nearest-neighbor (within a register or with a wheel) are iteratively swapped. For example, consider the initially ordered 10-qubit register: (1,2,3,4,5,6,7,8,9,10). During a first swap (or rotation) operation, each of the following swap operations are performed: $\{\{1,2\}, \{3,4\}, \{5,6\}, \{7,8\}, \{9,10\}\}$, where the integers refer to the positions of the pairs of qubits that are being simultaneously swapped. After the first swap operation, the updated order of the register is: (2,1,4,3,6,5,8,7,10, 9). These swap operation may be referred to as odd-pair swap operation, because the lower position qubit in each nearest-neighbor pair of swapped bits is positioned at an odd position within the register and the higher positioned qubit is positioned at an even position. A next swap operation may swap the alternating positions of qubits: $\{\{2,3\}, \{4,5\}, \{6,7\}, \{8,9\}\}$, where the integers refer to the positions of the pairs of qubits that are being simultaneously swapped. After the second swap operation, the updated order of the register is: (2,4,1,6,3,8,5,10,7,9). These swap operation may be referred to as even-pair swap operations, because the lower position qubit in each nearest-neighbor pair of swapped bits is positioned at an even position within the register and the higher positioned qubit is positioned at an odd position. The evolution of the logical ordering of the register may be notated as:

$$\begin{pmatrix} 1,2,3,4,5,6,7,8,9,10 \\ 2,1,4,3,6,5,8,7,10,9 \\ 2,4,1,6,3,8,5,10,7,9 \end{pmatrix},$$

as the descending rows show the updating of the order of the set of qubits. Similar operations, notations, and terminologies may be employed when discussing wheel rotations or swapping operations.

The various embodiments iteratively apply swap operators, which may be implemented swap gates 130-136 of FIG. 1B on the N qubits. The swap gates may be implemented in one or more networks of swap gates (i.e., swap networks). The iterative swap operations and/or swap networks may be configured to render each of the possible $$\binom{N}{2}$$

2-qubit pairings as a logically nearest-neighbor pair at least once and each of the possible $$\binom{N}{4}$$

4-quibit combinations as a grouping of four logically consecutive qubits. Thus, the Hamiltonian operators need to operate only on groupings of local qubits (e.g., pairs of nearest neighboring qubits and/or groups of four consecutive qubits). That is, the 2-qubit (non-local) time-evolution operators applied to simulate the non-local 1-body Hamiltonian terms need only operate on two nearest-neighbor pairings of qubits. Similarly, the 4-quibit (non-local) time-evolution operators applied to simulate the non-local 2-body Hamiltonian terms need only operate on four nearest-neighbor groupings of qubits. That is, the 2-qubit and 4-qubit quantum circuits need only to act on local parings (i.e., nearest neighboring qubits) or localized groupings (i.e., consecutive in position) of four qubits.

Furthermore, the swap operators need only to act locally, on qubits that are at most logically separated by three qubits (i.e., k≤4 as shown in swap gates 130-136 of FIG. 1B). Thus, the swap operators may be also somewhat localized. More specifically, all the non-local many-body interactions may be computed via local 2- and 4-qubit quantum circuits and nearest-neighbor swaps gates (e.g., swap gates 130-136). By configuring the swap networks for parallel qubit swaps and localizing the circuits and gates, the simulations of non-local interactions may be parallelized, reducing the circuit depth and the computational time. Architectures for qubit swap operations are discussed below for 2-body, 3-body, and 4-body interaction operators. However, other embodiments are not so constrained, and higher order terms may be computed via generalizing the networks of swap operations discussed herein. That is, the various embodiments may be readily generalized for k-body interactions, where k is any integer greater than 1.

Localizing 2-Qubit Pairs (i.e., k=2)

The below discussion for k=2 embodiments is directed towards qubit swap operations. However, as noted throughout, the various embodiments are not so constrained, and the swap operations may include fermionic swap operations. Various qubit swap networks will now be discussed. A swap network may include a plurality of swap gates (e.g., swap gates 130-136 of FIG. 1B) that perform the various qubit swap operations discussed. A swap network may include parallelized swap gates to simultaneously (or near simultaneously swap) multiple pairs of qubits. Each discrete swap gate may act on two of the N qubit lines in a quantum circuit.

Figure 3A:
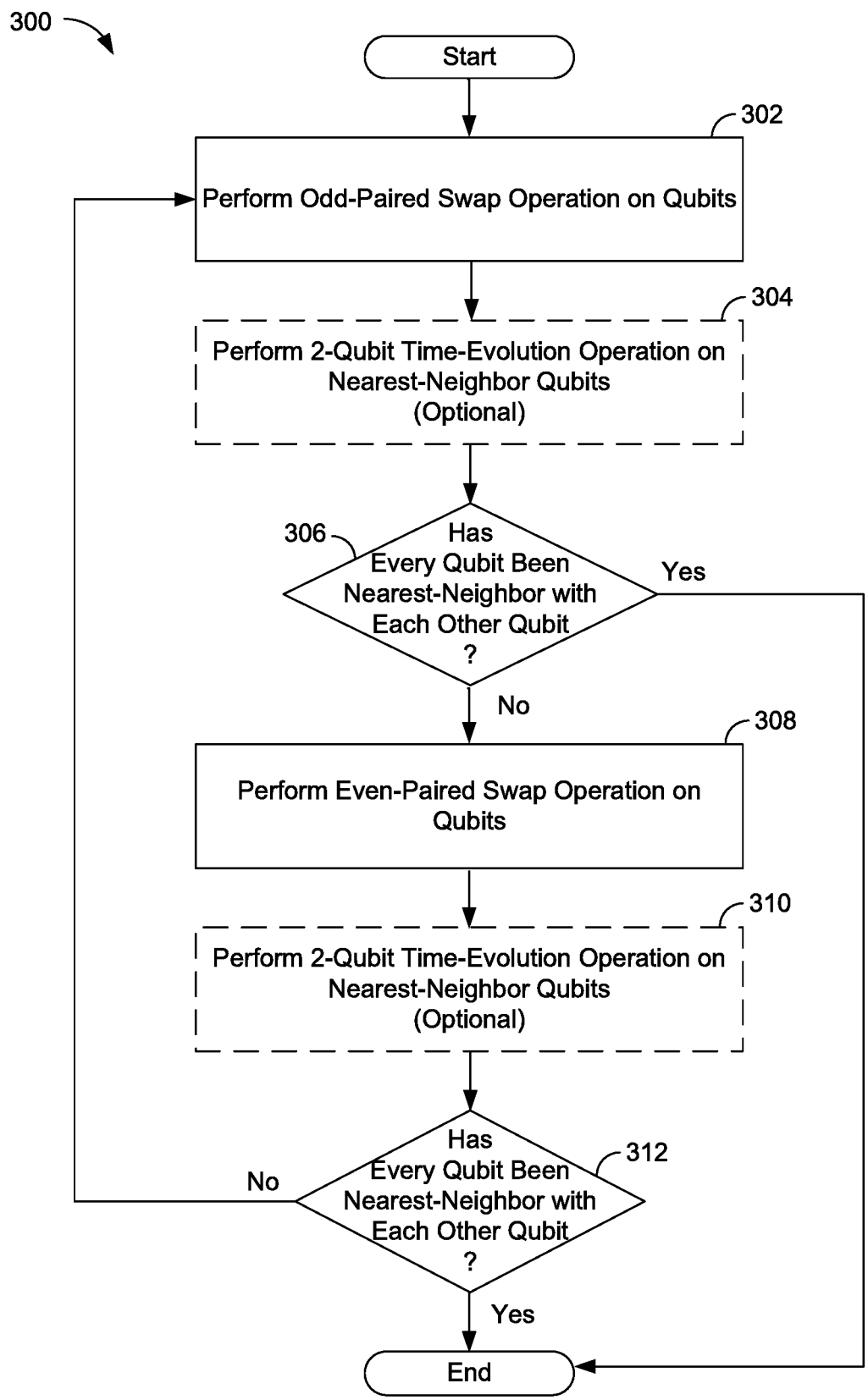
FIG. 3A provides a flow diagram that illustrates a process of qubit swap operations implemented by a 2-qubit pair swap network that is consistent with the various embodiments.
Figure 3B:
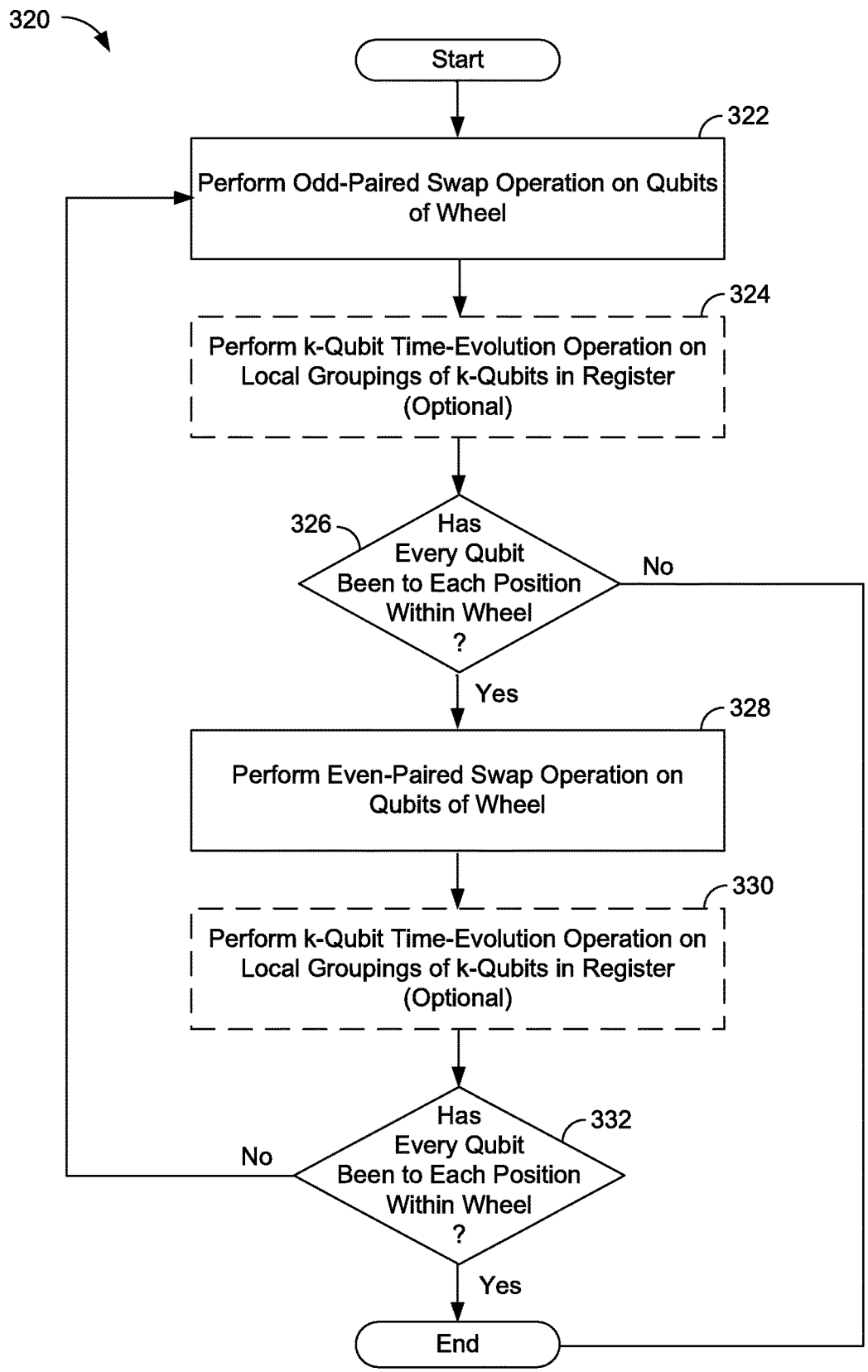
FIG. 3B provides a flow diagram that illustrates a process of qubit swap operations implemented by a wheel swap network that is consistent with the various embodiments.
Figure 3C:
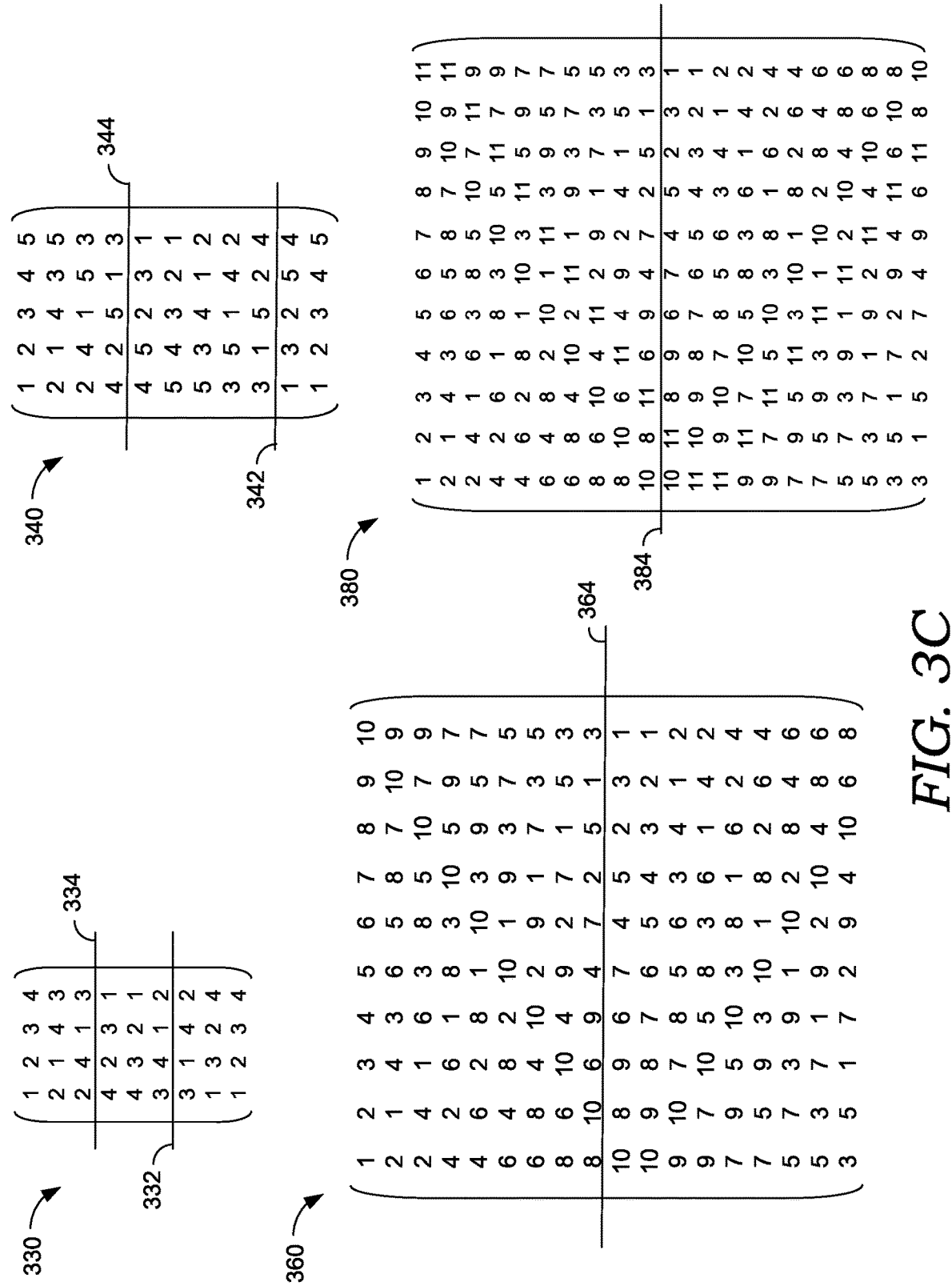
FIG. 3C shows the rotational operations of the processes of FIG. 3A-3B, as implemented via one or more qubit swap networks, for N=4, N=5, N=10, and N=11 qubit registers or qubit wheels.

FIG. 3A provides a flow diagram that illustrates a process 300 of operations of a 2-qubit pair swap network. FIG. 3B provides a flow diagram that illustrates a process 320 of operations of a wheel swap network. As noted, both a 2-body swap network and a wheel swap network may be implemented via systematic applications of swap gates 130-136 of FIG. 1B. That is, each of process 300 and 320 may be physically implemented via implanting a corresponding configuration of swap gates (i.e., a swap network) within a quantum computer being employed to simulate the time-evolution operators discussed herein. Processes 300 and 320 will be discussed in conjunction with FIG. 3C. FIG. 3C shows rotational operations of the qubit swap networks that implement processes 300 and 320 of FIGS. 3A-3B for N=4, N=5, N=10, and N=11 qubits. The below discussion of processes 300 and 320 are directed towards qubit swap operations. However, as noted throughout, the various embodiments are not so constrained, and the swap operations discussed throughout may include fermionic swap operations.

A 2-qubit pair swap network, such as one that implements process 300 of FIG. 3A, applies swap operations on nearest-neighbor pairs of the N qubits of a register (or n qubits of a wheel), such that each of the $$\binom{N}{2}$$

2-qubit pairs is a nearest-neighbor (or adjacent) pair at least once during process 300. Because each 2-qubit pair is a nearest-neighbor pair at least once during an implementation of process 300, a localized 2-qubit time-evolution circuit may operate on each pair of the possible $$\binom{N}{2}$$

pairings, to simulate each of the non-local interactions via a localized pair of qubits. It can be shown that the swap depth of a 2-qubit pair swap network is: $d_2(N)=N-1$. That is, via process 300, when the register (or wheel) is rotated through N-1 configurations (including its initial configuration), each of the N qubits will have been nearest-neighbors with each of the other N-1 qubits.

A wheel swap network, such as one that implements process 320 of FIG. 3B, applies swap operations on pairs of the n qubits of a wheel, such that each of the n qubits reaches each of the n positions within the wheel at least once. Each of the swap operations are performed on nearest-neighbor pairs within the wheel. However, nearest-neighbor pairs within a wheel may not be nearest-neighbor pairs within the register. That is, a wheel swap network may operate on non-adjacent bits within a register. However, in embodiments where, 2≤k≤4, two nearest-neighbor qubits of a wheel are separated at most by 3 intervening qubits. Thus, the swap gates 130-136 may be employed to implement a wheel swap network. It can be shown that the swap depth of a wheel swap network is:

$$d_w(n) = 2\left\lfloor \frac{n-1}{2} \right\rfloor + n = 2n - 2 + \mathrm{mod}(n, 2).$$

That is, via process 320, when the register (or wheel) is rotated through 2n-2+mod(n, 2) configurations (including its initial configuration), each of the n qubits will have been at each of the wheel's logical n positions at least once during an implementation of process 320.

Process 300 and 320 are similar processes, in that each process 300 and 320 iteratively applies parallelized alternating odd-pair and even-pair swap operations on the qubits. Process 300 and process 320 differ in their termination criteria. Process 300 may be terminated when each qubit has been a nearest-neighbor qubit to each other qubit at least once: $d_s(N)=N-1$. Process 320 may be terminated when each qubit has visited each position within its wheel at least once: $d_w(n)=2n-2+\mathrm{mod}(n, 2)$. Each of processes 300 and 320 include an iterative loop that alternatives between odd-paired and even-paired swap operations. As noted, the terminating condition for the iterative loop of process 300 is that every qubit has been a nearest-neighbor qubit with every other qubit at least once during process 300, which deterministically occurs with a swap depth of: $d_s(N)=N-1$. The terminating condition for the iterative loop of process 320 is that every qubit has been to each position within its wheel at least once during process 320, which deterministically occurs with a swap depth of: $d_w(n)=2n-2+\mathrm{mod}(n, 2)$. As shown in FIGS. 3A and 3B, processes 300 and 320 include decision blocks (i.e., blocks 306 and 312 for process 300 and blocks 326 and 332 for process 320) that check whether the terminating condition is met. Because the terminating conditions occur via deterministically determined swap depths, these decision blocks are optional. That is, processes 300 and 320 are not required to check whether the terminating condition has occurred because it deterministically occurs, via the above respective swap depths. These decision blocks are included for illustrative purposes, and are not required to be implemented.

Process 300 begins, after a start gate, at block 302 where each odd-paired nearest-neighbor pair of qubits is swapped. The multiple swaps may be parallelized via a parallelized 2-quibit pair swap network. For example, on a first iteration of block 302, implemented via a parallelized 2-qubit swap network for a N=10 register, transforms the register from its initial ordering of (1,2,3,4,5,6,7,8,9,10) to an updated ordering of (2,1,4,3,6,5,8,7,10,9), where a swap operation has been applied to each of the odd-pairs of nearest neighbor qubits. At optional block 304, a 2-qubit operator, such as but not limited to $e^{-iH_{pq}t}$, may be applied to each nearest-neighboring pair of qubits. At decision block 306, the terminating condition for a 2-qubit pair swap network is checked. That is, at decision block 306, it may be determined whether each qubit has been a nearest-neighbor (or adjacent) to each other qubit in the register. As discussed above, this occurs after $d_2(N)=N-1$ configurations of the register. If the terminating condition is not met, then process 300 flows to block 308. Otherwise, process 300 may be terminated at the end block.

At block 308, each even-paired nearest-neighbor pair of qubits may be swapped. Similarly to the odd-paired swaps, the multiple even-paired swaps may be parallelized. Continuing the above example, a first iteration of block 308 transforms the register from its second arrangement of (2,1,4,3,6,5,8,7,10,9) to a third arrangement of (2,4,1,6,3,8,5,10,7,9), where a swap operation has been applied to each of the even-pairs of nearest neighbor qubits. At optional block 310, the 2-qubit operator may be applied to each nearest-neighboring pair of qubits. At decision block 312, the terminating condition for a 2-qubit pair swap network is checked. If the terminating condition is not met, then process 300 returns to block 302. Otherwise, process 300 may be terminated at the end block.

Process 320 begins, after a start gate, at block 302 where each odd-paired grouping of qubits within the wheel is swapped. At optional block 324, a k-qubit operator, such as but not limited to $e^{-iH_{pqrs}t}$ may be applied to localized groupings of k qubits. Such operators may be implemented via quantum circuits, such as but not limited to circuits 210, 220, 230, 240, or 250 of FIGS. 2A-2E. At decision block 326, the terminating condition for wheel swap network is checked. That is, at decision block 326, it may be determined whether each qubit has visited each position within the wheel. As discussed above, this occurs after $d_w(n)=2n-2+\mod(n, 2)$ configurations of the wheel. If the terminating condition is not met, then process 320 flows to block 328. Otherwise, process 320 may be terminated at the end block.

At block 328, each even-paired nearest-neighbor pair of qubits may be swapped. Similarly to the odd-paired swaps, the multiple even-paired swaps may be parallelized At optional block 330, the k-qubit operator may be applied, similar to optimal block 324. At decision block 322, the terminating condition for a wheel swap network is checked. If the terminating condition is not met, then process 320 returns to block 322. Otherwise, process 320 may be terminated at the end block.

FIG. 3C shows the rotational (or parallelized swap) operations of both of processes 300 and 320, as implemented via a 2-qubit pair swap network and a wheel swap network, respectively, for N=4, N=5, N=10, and N=11 qubit registers and/or wheels. More specifically, swap or rotational operations 330 are for N=4, swap operations 340 are for N=5, swap operations 360 are for N=10, and swap operations 380 are for N=11. Within the various matrices, the rows indicate an arrangement (or logical ordering) of the qubits within a register and/or wheel, where the integers indicate the qubits indices. The transition from a row to the row directly underneath it indicates one rotational operation implemented via a 2-qubit swap network or a wheel swap network, e.g., blocks 302 or 308 of process 300 and/or blocks 322 or 328 of process 320. When discussing a 2-qubit swap network and/or process 300, the rows may indicate the arrangement of a register qubits. When discussing a wheel swap network, the rows may indicate the arrangement of a wheel of qubits.

For N=4 of operations 330, $d_2(4)=3$ and $d_w(4)=6$. The horizontal bar 334 and horizontal bar 332 indicate a termination of process 300 (e.g., operations of a 2-qubit swap network) and process 320 (e.g., operations of wheel swap network) respectively, for N=4. The extra rotational operations below horizontal bar 332 indicate how additional rotational operations may return the register and/or wheel to its initial arrangement of qubits. For N=5 of operations 340, $d_2(5)=4$ and $d_w(5)=9$. The horizontal bar 344 and horizontal bar 342 indicate a termination of process 300 and process 320, respectively, for N=5. The extra rotational operations below horizontal bar 342 indicate how additional rotational operations may return the register and/or wheel to its initial arrangement of qubits. For N=10 of operations 360, $d_2(10)=9$ and $d_w(10)=19$. The horizontal bar 364 indicates a termination of process 300. For operations 360, process 320 terminates at the last row. For N=11 of operations 380, $d_2(11)=10$ and $d_w(11)=21$. The horizontal bar 384 indicates a termination of process 300. For operations 380, process 320 terminates at the last row.

Note the general pattern in these register/wheel rotations, where initially, odd-indexed qubits travel towards the Nth position within the wheel and even-indexed qubits travel towards the $1^{st}$ position within the wheel. When a qubit reaches the $1^{st}$ or Nth (i.e., a boundary) position of the register/wheel, the qubit sits at the boundary position for two swap iterations, and then travels back towards the opposite boundary position in the register/wheel. As a qubit travels towards the Nth position of the register/wheel, the qubit may be referred to as an ingoing qubit, while as the qubit travels towards $1^{st}$ position of the register/wheel, the qubit may be referred to as an outgoing qubit. Also note that when each qubit reaches either the $1^{st}$ or Nth position of the register/wheel, the qubit sits at that position for two swap iterations and then changes direction of travel.

Via process 300, implemented by a 2-qubit swap network, each qubit will be a nearest neighbor to every other qubit, at least once, within a rotation depth of N-1. Via process 320 implemented by a wheel-swap network, each qubit will reach every position within the register/wheel, at least once, when the second to the last initially ingoing qubit reaches the Nth position. The initially ingoing qubits are even-indexed qubits. Thus, each qubit will have visited each position when the second to the last even-indexed position reaches the Nth position. For N=4, the second to the last even-indexed qubit is qubit 2, for N=5, the second to last even-indexed qubit is qubit 4, for N=10, the second to the last even-indexed qubit is qubit 8, and for N=10, the second to the last even-indexed qubit is qubit 10. Thus, the rotation of the register/wheel, via process 320, may be terminated when qubit 2, 4, 8, or 10 reaches the Nth position for the N=4, 5, 10, or 11 registers/wheels, respectively. Rotations under horizontal lines 332 and 334 show that additional register/wheel rotations be employed to return the ordering of the qubits back to its initial ordering. It should be noted that returning the qubits to the initial position may not be required in the embodiments.

Via each of process 300 and 302, each 2-qubit term may be operated on via a nearest-neighbor pair of qubits for all N. Furthermore, the operations may be parallelized, via a network of parallelized swap gates, to reduce the circuit depth. The embodiments of processes 300 and 320 discussed in conjunction with 2-qubit swap networks and wheel swap networks may be recursively employed to achieve k-qubit non-local interactions, where k is an integer greater than 2, via localized groupings of qubits. More specifically, the concept of a 2-qubit pairs and wheel swap networks may be combined with vectorization of qubits and rotations/permutations of the vectorized configurations of qubits to achieve non-local interactions, via groupings of localized (i.e., consecutive in position) k-qubits.

Localizing 3-Qubit Combinations (i.e., k=3)

The below discussion for k=3 embodiments is directed towards qubit swap operations. However, as noted throughout, the various embodiments are not so constrained, and the swap operations may include fermionic swap operations. Three-qubit interactions (i.e., k=3) will now be discussed. For 3-qubit interactions, each of the $$\binom{N}{3}$$

unique combinations of three qubits are considered. Similar to the k=2 embodiments, a swap network is employed to iteratively swap qubits such that each non-local 3-qubit interaction is rendered as a local interaction, via three local (i.e., logically consecutive) qubits. As discussed below, the k=3 embodiments may be recursively employed to render all non-local 4-qubit (i.e., k=4) interactions as a local interaction, via four local (i.e., logically consecutive) qubits. As discussed above, molecular chemistry orbital simulations may be achieved via a summation over the k=2 and k=4 terms. The k=2, k=3, and k=4 embodiments may be generalized to any higher value of k.

For k>2, the qubits of a register may be arranged in a vectorized configuration. For such a vectorized configuration, each of the N qubits may be classified as belonging to one of k classes. Thus, each qubit is labeled with a unique index and a class label, where the indexes of the qubits are a unique ID of each of the N qubits and one or more qubits are assigned to each of the k qubit classes. In contrast to unique qubit indexes, a plurality of qubits may be labeled with the same class. Thus, there are N unique qubit indexes, and k classes of qubits, where k<N. Thus for k=3, in addition to a unique qubit index, each qubit will be assigned one of classes 1, 2, or 3. The qubits will be labeled in a cyclic fashion. For a 14-qubit register, the 14 qubits may be labeled and ordered as $(1_1, 2_2, 3_3, 4_1, 5_2, 6_3, 7_1, 8_2, 9_3, 10_1, 11_2, 12_3, 13_1, 14_2)$, where the normal font-sized integer indicates the unique index of the qubit and subscript integer indicates the qubit's class (i.e., 1, 2, or 3).

A separate qubit wheel may be formed for each class comprising the qubits assigned to the class. Because each qubit is assigned exactly one class, the formation of the class generates k disjoint subsets of the N qubits For example, for the 14-qubit register, the class 1 wheel includes qubits: $(1_1, 4_1, 7_1, 10_1, 13_1)$, the class 2 wheel includes qubits: $(2_2, 5_2, 8_2, 11_2, 14_2)$, and the class 3 wheel includes qubits: $(3_3, 6_3, 9_3, 12_3)$. For a N-qubit register, the depth of qubit wheel_1 is computed as:

$$n_1 = \left\lceil \frac{N}{3} \right\rceil,$$

the depth of qubit wheel_2 is $$n_2 = \left\lfloor \frac{N}{3} \right\rfloor + \delta_{N,mod(3,2)},$$

and the depth of qubit wheel_

3 is $n_3 = \left\lfloor \frac{N}{3} \right\rfloor.$

Note that $n_1 \geq n_2 \geq n_3$ for all N.

Each of the $$\binom{N}{3}$$

3-qubit interactions may computed via groupings of local (i.e., logically consecutive within the register) 3-qubit combinations. For example, all unique combinations of one qubit from class 1, one qubit from class 2, and one qubit from class 3 must be acted on by quantum circuit that simulates the time evolution operator for k=3. The notation of 123 is adopted to indicate a specific type of a 3-qubit combination, where one qubit is from class 1, one qubit is from class 2, and one qubit is from class 3. For instance, the combinations of (1,2,3), (4,5,6), and (7,8,9) are 3-qubit combinations of the 3-qubit combination type indicated as 123, as well as the combinations of (1,5,9), (4,8,12), and (13,11,3). Note that there are $n_1 \cdot n_2 \cdot n_3$ unique combination of qubits in the 123 type 3-qubit combination. Generalizing this notation, all unique 3-qubit combinations of combination types 122 (e.g., (4,2,11)) and 133 (e.g., (10,3,9)) combinations must be acted upon by a time-evolution operated implemented via a quantum circuit, as well as the combinations classes of 211 (e.g., (8,4,13)), 233 (e.g., (14,6, 12)), 311 (e.g., (6, 1,10)), and 322 (e.g., (12, 52, 14)) qubits. Similarly, all combinations of combination types 111 (e.g., (4, 10, 13)), 222 (e.g., (2,8,11)), and 333 (e.g., (3,6,9)) must be acted upon via a quantum circuit.

The 3-qubit combination types may be categorized into 5 categories based on symmetries of the qubit combinations types of qubit classes. For example, in view of the symmetry between qubit combination types 122 and 133, these qubit combination types may be categorized as a category with member qubits combination types 122 and 133. Likewise, qubit combination types 211 and 233 may be categorized together, qubit combination types 311 and 322 may be categorized together, and qubit combination types 111, 222, and 333 may be categorized together.

FIG. 4A provides a table 400 that illustrates various properties for the class types of a 3-qubit interactions that is consistent with the various embodiments presented herein. More particularly, each row of table 400 corresponds to a category of qubit combination type. Note for k=3, category 0 corresponds to 123 type combinations and category 4 includes member types 111, 222, and 333. Categories 1, 2, 3, each include member types with a single qubit from the wheel indicated by the category, and two qubits from one of the other two wheels. The first column of table 400 indicates the category of the 3-qubit combination types. The second column of table 400 indicates the combination type members included in the category of the row. The third column of table 400 indicates the number of unique 3-quibit combinations included in the categories. Note that the calculations in this column assume that N is divisible by 3. For large N, $$\frac{N}{3} \approx \left\lfloor \frac{N}{3} \right\rfloor \approx \left\lceil \frac{N}{3} \right\rceil,$$

and thus any error attributed to this assumption is small. The fourth column of table 400 indicates the ratio of 3-qubit combinations for the category (as indicated by column 3) to the total number of 3-qubit combinations, for large N. As will be explained below, the fifth column of table 400 indications depth of wheel rotations (e.g., qubit swap operations) required to render all 3-qubit combinations as groupings of three local (i.e., consecutive) qubits.

FIG. 4B provides a table 410 that illustrates vectorizations of a 3-qubit configuration for 5≤N≤10 that is consistent with the various embodiments presented herein. Each row of table 410 corresponds to a separate value of N, where the value of N is indicated in the first column. The second, third, fourth, and fifth columns of table 410 correspond to the category 0, category 1, category 2, and category 3 of 3-qubit combination types. Each entry in the table provides a vector (of length N) for the corresponding value of N and combination type category. As will be discussed below, the vector indicates an arrangement of combination types to achieve each of the $$\binom{N}{3}$$

3-qubit interactions.

Figure 4C:
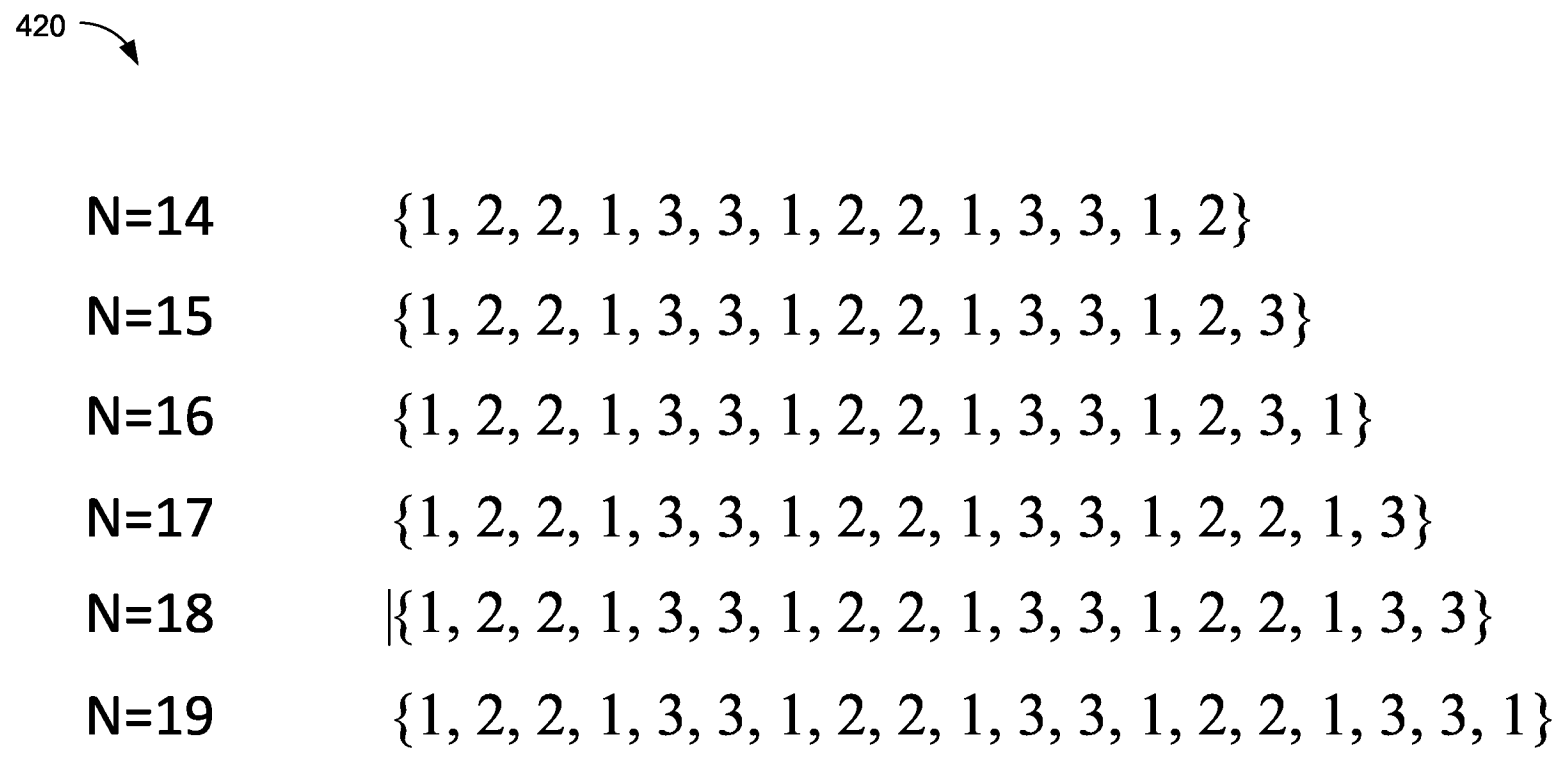

Briefly here, the vectorization for a category of combination types indicates the classes of qubits which should be arranged (or swapped into) the corresponding position of the register to achieve each of the number of unique 3-qubit combinations for the combination types that are members of the corresponding category of combination types. For example, as discussed below in conjunction with at least FIGS. 5A-5B, to achieve each of the possible 3-qubit combinations, via local groupings of 3 qubits, for N=8, the 8 qubits are arranged such that the qubit classes, within the register, are ordered via the following vector: [1,2,3,1,2,3, 1,2], where the integers indicate qubit type, and not qubit index. One possible such qubit arrangement within the 8-qubit register is the initial qubit ordering of: (1,2,3,4,5,6, 7,8), where the integers refer to the qubit indexes. As another example, for category 1 of N=8, the 8 qubits are arranged such that the qubit classes, within the register, are ordered as the following vector: [1,2,2,1,2,3,3,1]. One possible such qubit arrangement within the 8-qubit register is the initial qubit ordering of: (1,2,5,4,8,3,6,7). The vectorization patterns of the various combination types (and categories) are apparent from the symmetry of table 410. Table 420 of FIG. 4C shows non-limiting embodiments of the vectorization for category 1 for N=14,15,16,17,18, and 19. That is, table 420 provides various embodiments for the vectorizations for larger N values than is provided in table 400 o FIG. 4A. Table 430 of FIG. 4D shows still other non-limiting embodiments of the vectorization for category 1 for N=14,15,16, 17,18, and 19. The vectorizations shown in tables 420 and 430 are non-limiting, and other vectorizations may be employed. For example, in an alternative vectorization for N=17, which not shown in FIG. 4C or FIG. 4D, is {1,2,2, 1,2,2,1,2,2,1,3,3,1,3,3,1,3}.

Note that the embodiments of 3-qubit vectorizations shown in table 410 of FIG. 4B are non-limiting, and other vectorizations are possible. Thus, the embodiments are not constrained via the vectorizations shown in table 410. As a non-limiting example, in some embodiments, the vectorization for N=6, category 1 could include the vector: [1,3,3,1, 2,2], rather than the vector: [1,2,2,1,3,3], as shown in table 410. As additional non-limiting examples, the vectorization for N=10, category 2 could alternatively include the vector: [1,1,2,1,1,2,3,3,2,3] and the vectorization for N=10, category 3 could alternatively include the vector: [1,1,3,1,1,3, 2,2,3,2]. That is, for category 2 and/or 3, the pattern "1,2,2" may be repeated until the wheel_2 qubits are used up, and then the pattern of "3,3,1" is employed.

Figure 5A:
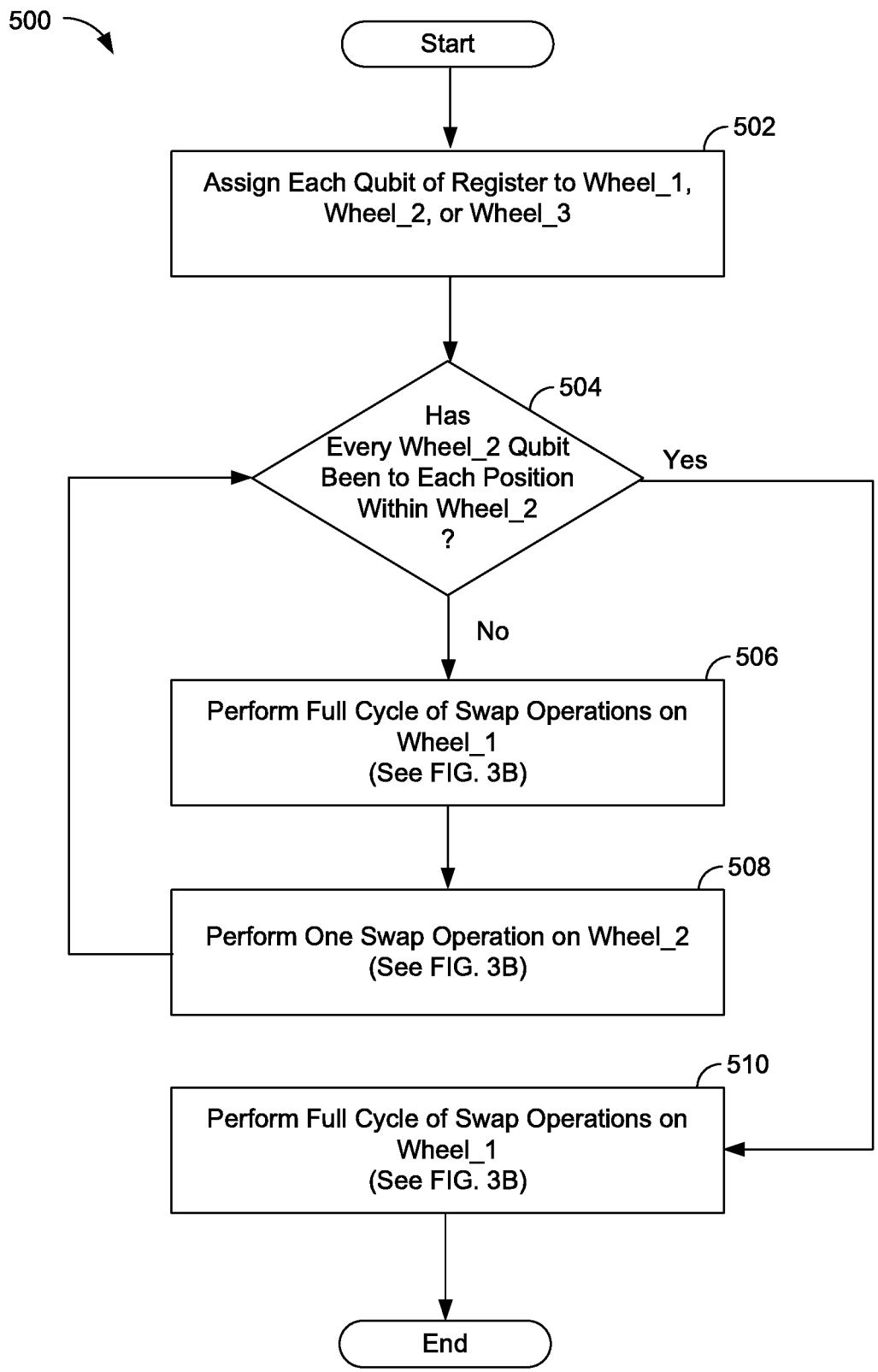
FIG. 5A provides a flow diagram that illustrates a process implementing qubit swap operations to localize all category 0 3-qubit combinations within a quantum computer.

FIG. 5A provides a flow diagram that illustrates a process 500 of operations of wheel swap network to localize all 123 type 3-qubit combinations (i.e., category 0) within a quantum computer. FIG. 5B shows the operations of process 500 for an N=8 qubit quantum computer. FIGS. 5A-5B will be discussed together. The below discussion of FIGS. 5A-5B is directed towards qubit swap operations. However, as noted throughout, the various embodiments are not so constrained, and the swap operations may include fermionic swap operations.

Swap operations 520 of FIG. 5B show the iterative wheel rotational operations of process 500 on an N=8 qubit register, subdivided into 3 qubit wheels. The matrix notation of operations 520 indicate the dynamics of the qubit swapping (i.e., rotations) of each iterative step of process 500 for N=8. In the following discussion, a single rotation operation of a wheel may refer to one parallelized odd-paired or even-paired swap of the nearest neighbor pairs within the wheel. That is, a single wheel rotation may include a parallelized odd-paired or even-paired swap operation of the wheel that corresponds to an execution of one of: block 322 or block 328, each of process 320 of FIG. 3B. A full rotation of a wheel may correspond to full execution of process 320. If the depth of a wheel is $d_w(n)$, then the wheel must transition through n arrangements (or re-orderings) for a full rotation. Thus, starting from an initial arrangement (or order), it generally takes n−1 single swap operations for each qubit to visit each position within the wheel.

Process 500 includes an iterative loop that alternatives between odd-paired and even-paired swap operations. As noted, the terminating condition for the iterative loop of process 500 is that every qubit has been to each position within its wheel at least once during process 500, which deterministically occurs with a swap depth of: $d_w(n)=2n-2+\mod(n, 2)$. As shown in FIG. 5A, process 500 includes a decision block (i.e., block 504) that checks whether the terminating condition is met. Because the terminating condition occurs via deterministically determined swap depths, this decision block is optional. That is, process 500 is not required to check whether the terminating condition has occurred because it deterministically occurs, via the deterministically determined swap depth. This decision block is included for illustrative purposes, and is not required to be implemented.

Process 500 begins, after a start block, at block 502, where each of the N qubits is assigned to one of wheel_1, wheel_2, or wheel_3. As shown in FIG. 5B, for N=8, wheel_1 530 includes qubits [1,4,7], wheel_2 540 includes qubits [2,5,8], and wheel_3 560 includes qubits [3,6]. Thus, $n_1=3$, $n_2=3$, and $n_3=2$. The corresponding dynamics of the qubit swapping, at the level of each wheel, are shown in the corresponding rows and columns to the right of operations 520. Process 500 includes wheel swap networks iteratively operating on wheel_1 and wheel_2 to achieve each category 0 3-qubit combination as a local grouping. As shown in FIGS. 5A-5B, the wheel swap network operating on wheel_1 may be nested in and/or be executed as a subroutine of the wheel swap network operating on wheel_2. To achieve each unique 3-qubit category 0 combination, wheel_3 need not be required to be rotated.

Because the wheel swap network operating on wheel_1 is a subroutine of the wheel swap network operating on wheel_2, for each arrangement (i.e., re-ordering) of wheel_2 (within the wheel depth of wheel_2), wheel_1 is fully rotated. That is, for each updating of the order of wheel_2, wheel_1 is fully rotated via process 320 of FIG. 3B, such that each qubit in wheel_1 visits each position within wheel_1 at least once. For N=8, the wheel depths for wheel_1 530 and wheel_2 540 are: $d_w(n_1)=d_w(n_2)=d_w(3)=5$. Thus, for a qubit to visit each location in either wheel_1 540 or wheel_2 540, the corresponding wheel has to transition through 5 arrangements (or orderings), which generally requires 5−1=4 single parallelized odd-paired or even-pared swap operations, i.e., single rotations. In FIG. 5B and for wheel_1 530, the boxes grouping five re-orderings of wheel_1 530 indicate a full rotation of wheel_1 530. Note that four parallelized swap operations (or four single rotations) of wheel_1 530 are required to fully rotation wheel_1 530. For wheel_2 540, the boxes group a single swap operation (i.e., a single rotation) of wheel_2 540. Note that similar to wheel-1 530, for a full rotation of wheel_2 540, wheel_2 540, four single parallelized swap operations (or single rotations) are required for each qubit to visit each position within wheel_2 540. The boxes for wheel_1 530 and wheel_2 540 indicate that the rotation of wheel_1 530 is a subroutine of the rotation of wheel_2 540. A full cycle of swap operations on a wheel may include a full rotation of the wheel and/or a full execution of process 320 on the wheel.

As also shown in FIG. 5B, the rotations of wheel_1 540 are cyclical with a period of 6 rotations: [1,4,7]→[4,1,7]→[4,7,1]→[7,4,1]→[7,1,4]→[1,7,4]→[1,4,7]. Via symmetry with wheel_1 530, the rotations of wheel_2 540 are also cyclical with a period of 6 rotations: [2,5,8]→[5,2,8]→[5,8,2]→[8,5,2]→[8,2,5]→[2,8,5]→[2,5,8]. In operations 520 of FIG. 5B and for N=8, all $n_1 \cdot n_2 \cdot n_3$=12 of 123 type (i.e., category 0) qubit combinations are achieved. As shown in the fifth column of table 400 of FIG. 4A, the depth of the nested rotations of wheel_1 and wheel_2 in process 500 (for category 0 combinations) is $d_w(n_1) \cdot d_w(n_2)$.

At decision block 504, it is determined whether the terminating condition for rotating wheel_2 is met. As discussed in conjunction with at least decision block 326 of FIG. 3B, at block 504, it is determined whether each qubit in wheel_2 has visited each position within wheel_2. As noted, wheel_2 has a swap depth of $d_w(3)=5$. Thus, the terminating condition for wheel_2 is met after four rotations of wheel_2. If wheel_2 has not been fully rotated, process 500 flows to block 506. Otherwise, process 500 flows to block 510.

At block 506, wheel_1 is fully rotated. Various embodiments for rotating wheel_1 are discussed in conjunction with at least process 320 of FIG. 3B. As noted above, the boxes grouping the re-orderings of wheel_1 530 in FIG. 5B show full rotations of wheel_1 530. At block 508, wheel_2 is rotated via one swap operation (via either parallelized odd-paired or even-paired qubit swap operations). The boxes grouping a single swap operation (or wheel rotation) of wheel_2 540 show one rotation of wheel_1. Process 500 returns to decision block 504. At block 510, another full cycle of swap operations and/or a full rotation of the wheel is required to generate all category 0 3-qubit combinations. Process 500 then terminates.

Figure 5C:
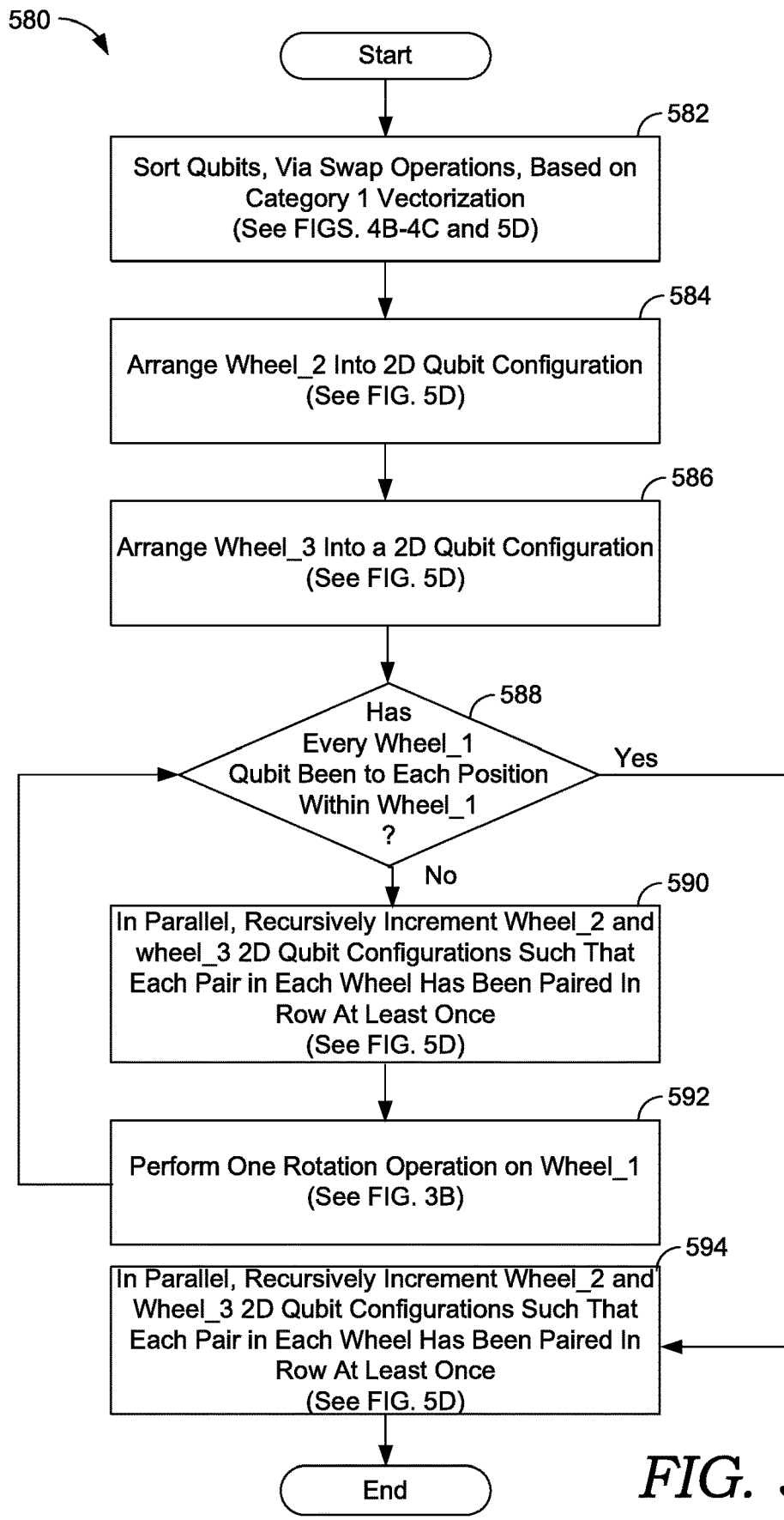
FIG. 5C provides a flow diagram that illustrates a process to localize all category 1 3-qubit combinations within a quantum computer.

As shown in FIG. 5B, process 500 enables the generation of each category 0 3-qubit combination. The 3-qubit combinations of category 1, 2, 3, and 4 must also be generated. FIG. 5C provides a flow diagram that illustrates a process 580 to localize all category 1 3-qubit combinations within a quantum computer. Because of symmetry between the categories 1, 2, and 3, process 580 may be generalized to all find all 3-qubit combinations of categories 2 and 3 substituting the corresponding wheels of those categories. Category 4 3-qubit combinations are discussed below.

Figure 5D:
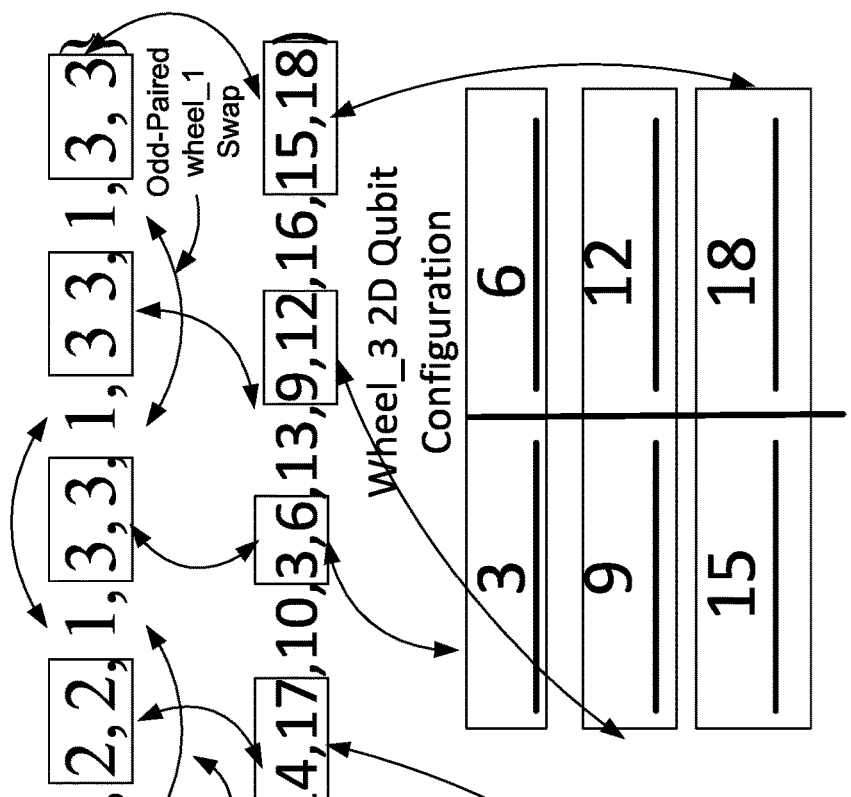
FIG. 5D illustrates an embodiment of a 2D qubit configuration utilized in the process of FIG. 5C that is consistent with the various embodiments.

FIG. 5D illustrates an embodiment of a 2D qubit configuration that is utilized in process 580 of FIG. 5C that is consistent with the various embodiments. Note that the 2D nature of the qubit configuration shown in FIG. 5D need not be a physical configuration of the qubits, but rather may be a logical construct. Accordingly, FIG. 5D will be discussed in conjunction with process 580 of FIG. 5C. The below discussion of FIGS. 5C-5D is directed towards qubit swap operations. However, as noted throughout, the various embodiments are not so constrained, and the swap operations may include fermionic swap operations. Process 580 includes an iterative loop that alternatives between odd-paired and even-paired swap operations. As noted, the terminating condition for the iterative loop of process 580 is that every qubit has been to each position within its wheel at least once during process 580, which deterministically occurs with a swap depth of: $d_w(n)=2n-2+\mod(n, 2)$. As shown in FIG. 5C, process 580 includes a decision block (i.e., block 588) that checks whether the terminating condition is met. Because the terminating condition occurs via deterministically determined swap depths, this decision block is optional. That is, process 580 is not required to check whether the terminating condition has occurred because it deterministically occurs, via the deterministically determined swap depth. This decision block is included for illustrative purposes, and is not required to be implemented.

After a start block, process 580 begins at block 582, where the qubits are sorted, into an order that is consistent with and/or based on the vectorization of category 1. FIGS. 4B, 4C, and 4D show the vectorizations for category 1. The patterns for these vectorizations may be generalized for higher values of N. Any qubit sorting routine may be employed to sort the qubits, via qubit swap operations. For example, after termination of process 500, the qubits will be ordered such that the wheels are interleaved. A bubble sort algorithm may be employed to sort the qubits into an order that is based on the vectorization for category 1. FIG. 5D shows a non-limiting example for N=18. The qubits assigned to each of the three wheels are shown. As indicated by table 420 of FIG. 4C, the vectorization for N=18 for category 1 may be: {1,2,2,1,3,3,1,2,2,1,3,3,1,2,2,1,3,3}. As indicated in table 430 of FIG. 4D, other alternative vectorizations are possible. The sorted register shows one possible sorting of the qubits based on the vectorization. Other orderings of the register are possible. In one embodiment, prior to block 582, the qubits may be returned to their initial positions via additional wheel rotations, and then sorted based on the vectorization. In FIG. 5D, the arrows grouping the boxes of same wheel qubits in the category 1 vectorization and the boxes in the sorted register show the correspondence between the vectorization and the sorting register, as generated via block 582. For N=18, $n_1=n_2=n_3=6$.

Process 580 generates each possible 122 and each possible 133 type of combinations. In various embodiments of process 580, wheel_1 is rotated via process 520 of FIG. 5B. Wheel_2 and wheel_3 may be configured as a 2D qubit configuration. The 2D qubit configurations for wheel_2 and wheel_3 are shown near the bottom of FIG. 5D. A 2D qubit configuration is a logical or virtual arrangement of the qubits that need not be a physical arrangement of the physical instantiation of the qubits. As shown in FIG. 5D, the 2D qubit configuration may include a 2D logical arrangement of the qubits that includes 2 columns and $\lceil \frac{n}{2} \rceil$ rows, where n is the number of qubits in the wheel. If n is odd, the last row will include only a single qubit.

A 2D qubit configuration may be somewhat similar to a 2-wheeled slot machine, where the vertical columns of the 2D qubit are similar to the wheels of the slot machine and the horizontal rows corresponds to the slots of the slot machine. Each of the horizontal rows corresponds to one of the nearest-neighbor pairs of the wheel within the register. As shown in FIG. 5D, for N=18, there are three horizontal rows for each of wheel_2 and wheel_3. Each of the horizontal rows corresponds to one of the two-qubit pairings of qubits from the same wheel that is based on the vectorization of category 1. In FIG. 5D, the arrows between the 2-qubit pairings in the sorted register and the horizontal rows demonstrate the correspondence.

Wheel_1 is rotated via parallelized swap operations, such that every qubit in wheel_1 visits each location within the register corresponding to the vectorization of category 1, at least once. In FIG. 5D, the parallelized odd-paired and even-paired swap operations of wheel_1 are shown as arrows in the category 1 vectorization. To achieve every 122 type combination, each of the possible $$\binom{n_2}{2}$$

2-qubit pairings of wheel_2 must appear consecutive in one of the horizontal rows of the wheel_2 2 D qubit configuration at least once during each arrangement of wheel_1. Similarly, to generate every 133 type combination, each of the possible $$\binom{n_3}{2}$$

2-qubit pairings of wheel_3 must appear consecutive in one of the horizontal rows of the wheel_3 2 D qubit configuration at least once during each arrangement of wheel_1. Accordingly, the qubits of the 2D qubit configurations may be incrementally swapped (e.g., via process 300 or process 320 of FIGS. 3A and 3B respectively), such that each pair in the wheel appears consecutive at one of the horizontal rows.

Thus, in process 580, wheel_1 is rotated, via process 320 of FIG. 3B. As a subroutine of the swap operations of wheel_1, the 2D qubit configurations of wheel_2 and wheel_3 may be incremented in parallel, generating each 122 and 133 type 3-qubit combination. It should be understood that process 580 may generate each of the 112, 233, 311, and 322 combinations by permuting the wheel that is rotated and the two wheels are arranged on the 2D qubit configuration. Thus, all 3-qubit combinations for categories 1, 2, and 3 may be generated via process 580.

Returning to FIG. 5C, at block 584, wheel_2 is logically arranged into a 2D qubit configuration. At block 586, wheel_3 is logically arranged into a 2D qubit configuration. One embodiment for a 2D qubit configurations for wheel_2 and wheel_3 is shown in FIG. 5D. At decision block 588, it is determined whether the terminating condition has been meet for wheel_1. That is, at block 588, it is determined whether each qubit within wheel_1 has been to each position of wheel_1. If so, then process 580 flows to block 594. Otherwise, process 580 flows to block 590. At block 590, the 2D qubit configurations of each of wheel_2 and wheel_3 is incremented, via swap operations, such that each of the possible $$\binom{n_2}{2}$$

2-qubit pairings of wheel_2 appears as a consecutive pair in one of the horizontal rows of the 2D qubit configuration of wheel_2 and each of the possible $$\binom{n_3}{2}$$

2-qubit pairings of wheel_3 appears as a consecutive pair in one of the horizontal rows of the 2D qubit configuration of wheel_3. Various embodiments of process 300 or process 320 may be employed to increment the 2D qubit configurations, via alternating parallelized odd-paired and even-paired swap operations, such that every pair in the wheel is a nearest neighbor pair and adjacent in one of the horizontal rows at least once. As noted, the increments to wheel_2 and wheel_3 may be parallelized, such that wheel_2 and wheel_3 are incremented together.

At block 592, one rotation operation, via either a parallelized odd-paired swap operation or a parallelized even-paired swap operation, is performed on wheel_1. At least a portion of process 320 of FIG. 3B may be employed to perform the rotation operation on wheel_1. Process 580 returns to decision block 588. At block 594, to generate the remaining 122 and 133 type 3-qubit groupings, associated with the final arrangement of wheel_1, the 2D qubit configurations of each of wheel_2 and wheel_3 is incremented, via swap operations, such that each of the possible $$\binom{n_2}{2}$$

2-qubit pairings of wheel_2 appears as a consecutive pair in one of the horizontal rows of the 2D qubit configuration of wheel_2 and each of the possible $$\binom{n_3}{2}$$

2-qubit pairings of wheel_3 appears as a consecutive pair in one of the horizontal rows of the 2D qubit configuration of wheel_3. Once all the localized 3-qubit groupings of category 1 have been generated, process 580 may terminate. Note that because the increments of wheel_2 and wheel_3 are parallelized in blocks 590 and 594, the 122 and 133 type combinations are generated in parallel.

The category 2 and category 3 localized 3-qubit combinations may be generated via a similar process that permutes the wheels. Thus, process 500 may generate the category 0 combinations and process 580 (and variants thereof) may generate the category 1, 2, and 3 combinations. Category 4 combinations may be generated via recursively employing processes 500 and 580. In exemplary and non-limiting embodiment. Upon generating each of the category 0, 1, 2, and 3 combinations, the register may be sorted (e.g., a parallel bubble sort) based on a category 4 vectorization of: $\{1,1,1, \ldots 1,1,1,2,2,2, \ldots, 2,2,2,3,3,3, \ldots, 3,3,3\}$. That is, the register may be sorted into three sub-registers, each sub-register holding the qubits of one of the three wheels. Processes 500 and 580 may recursively applied to each of the sub-registers, generating sub-sub-registers. The recursive application may continue until all category 4 localized 3-qubit combinations have been localized within each of the sub-registers. Note that the recursive application of processes 500 and 580 to generate the category 0, 1, 2, and 3 localized combinations within the sub-registers may be parallelized for increased efficiency and decreasing the depth of the swap networks required to generate the localized 3-qubit combinations. Upon terminating the recursion, each of category 0, 1, 2, 3, and 4 localized combination for 3-qubits has been generated.

Note that to implement the recursion required to generate the category 4 combinations, it may be shown that the depth of the required swap network is determined as: $d_3(n) = \frac{1}{4}(5n^2 - 26n + 16 \log_3 n + 21)$. Thus, as described in conjunction with at least FIG. 5E, the depth of the required swap network scales as $\mathcal{O}(N^2)$.

Figure 5E:
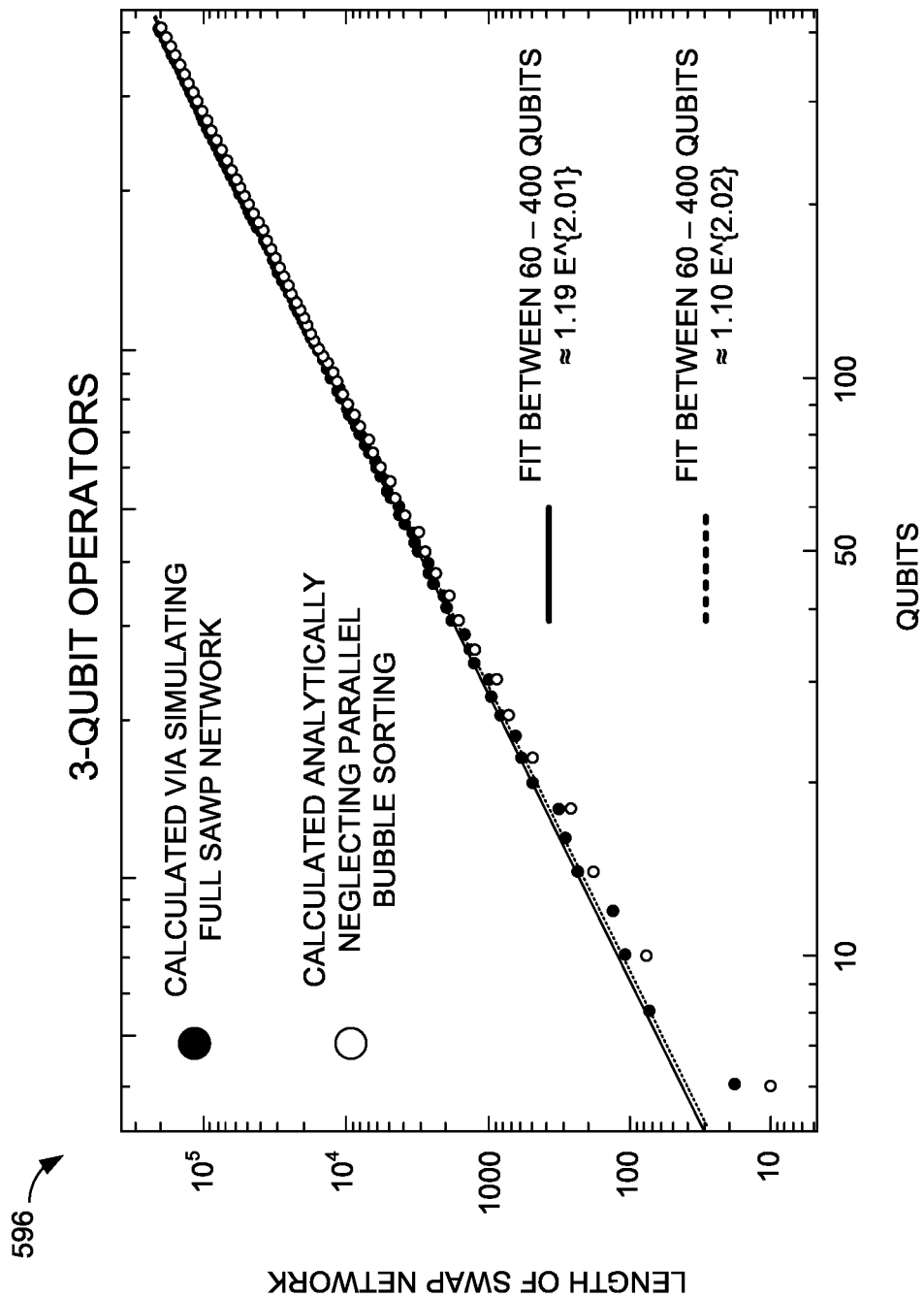
FIG. 5E provides a plot of numerical results indicating that the circuit depth for a swap network for 3-qubit operators scales approximately as $\mathcal{O}(N^2)$.

FIG. 5E provides a plot 596 of calculations indicating that the circuit depth for a swap network for 3-qubit operators scales approximately as $\mathcal{O}(N^2)$. For the solid circular discrete data points (•), the depth of the network, as a function of N, was calculated by simulating the swap operations with a full swap network that included the parallel bubble sort operations required to transition between the swap operations for the various categories of combination types. That is, for the solid data points, the swap operations discussed in conjunction with at least FIGS. 5A-5D, have been numerically simulated to generate each of the localized (i.e., logically consecutive in the register) 3-qubit pairs of the possible $$\binom{N}{3}$$

pairings for up to N=400. For the non-solid data points (○), the depth of the network was determined analytically, via expressions for the depth of swap operations required by the various categories shown in the fifth column of table 400 of FIG. 4A. For the non-solid data points, the contribution of the parallel bubble sort operations has been neglected. The solid line indicates a log-log linear regression fit to the solid data points. The hashed line indicates a log-log linear regression fit to the non-solid data points. For the solid line, the log-log linear fit is: $(1.19 \pm 0.03) \cdot 10^{2.007 \pm 0.004}$. For the hashed line, the log-log linear fit is: $(1.10 \pm 0.03) \cdot 10^{2.020 \pm 0.005}$. The linear fits to both methods (numerical simulation and analytic calculations) demonstrates that the depth of the swap network (or parallelized swap operations) scales as approximately $\mathcal{O}(N^2)$, and that the parallel bubble sorts do not drive the scaling of the required circuit depth.

Localizing 4-Qubit Combinations (i.e., k=4)

The below discussion for k=4 embodiments is directed towards qubit swap operations. However, as noted throughout, the various embodiments are not so constrained, and the swap operations may include fermionic swap operations. Each of the possible $$\binom{N}{4}$$

4-qubit combinations may be localized by recursively generating the localized 2-qubit and 3-qubit combinations as now discussed. That is, the various embodiments discussed at least in conjunction with FIGS. 3A-5E may be iteratively and recursively applied to localize the 4-qubit combinations. For k=4, the N qubits may be subdivided into four wheels: wheel_1, wheel_2, wheel_3, and wheel_4. The process of assigning qubits to the four wheels may be generalized from the process of assigning the qubits to three wheels. Furthermore, 4-qubit combination types may be generated, similar to that discussed with 3-qubit combination types, via the four wheels. For example, 4-qubit combination types include, but are not limited to: 1234, 1122, 1134, 1113, and 1111. Similar to the categories of 3-qubit combinations, by employing the symmetry of the combination types, the 4-qubit types may be organized into categories. Note that for k=3 embodiments, the third wheel need not be rotated, i.e., swap operations need not be performed on the qubits included in the wheel_3. Likewise, for k=4 embodiments, swap operations need not be performed on the qubits of wheel_4. According, in some embodiments, the generation of wheel_4 need not be required.

FIG. 6A provides a table 600 that illustrates various properties for the class types of a 4-qubit interactions that are consistent with the various embodiments presented herein. Table 600 is similar to table 400 of FIG. 4A, but is for 4-qubit combination, rather than 3-qubit combinations. The first column of table 600 shows that 15 categories of combination types exist for 4-qubit combinations, and column two indicates the members of each category. Each of the combination types may be referenced as: 1234, XXYY, XXYZ, XXXY, and XXXX, where the variables X, Y, and Z can take on the values of 1, 2, 3, or 4.

Figure 6B:
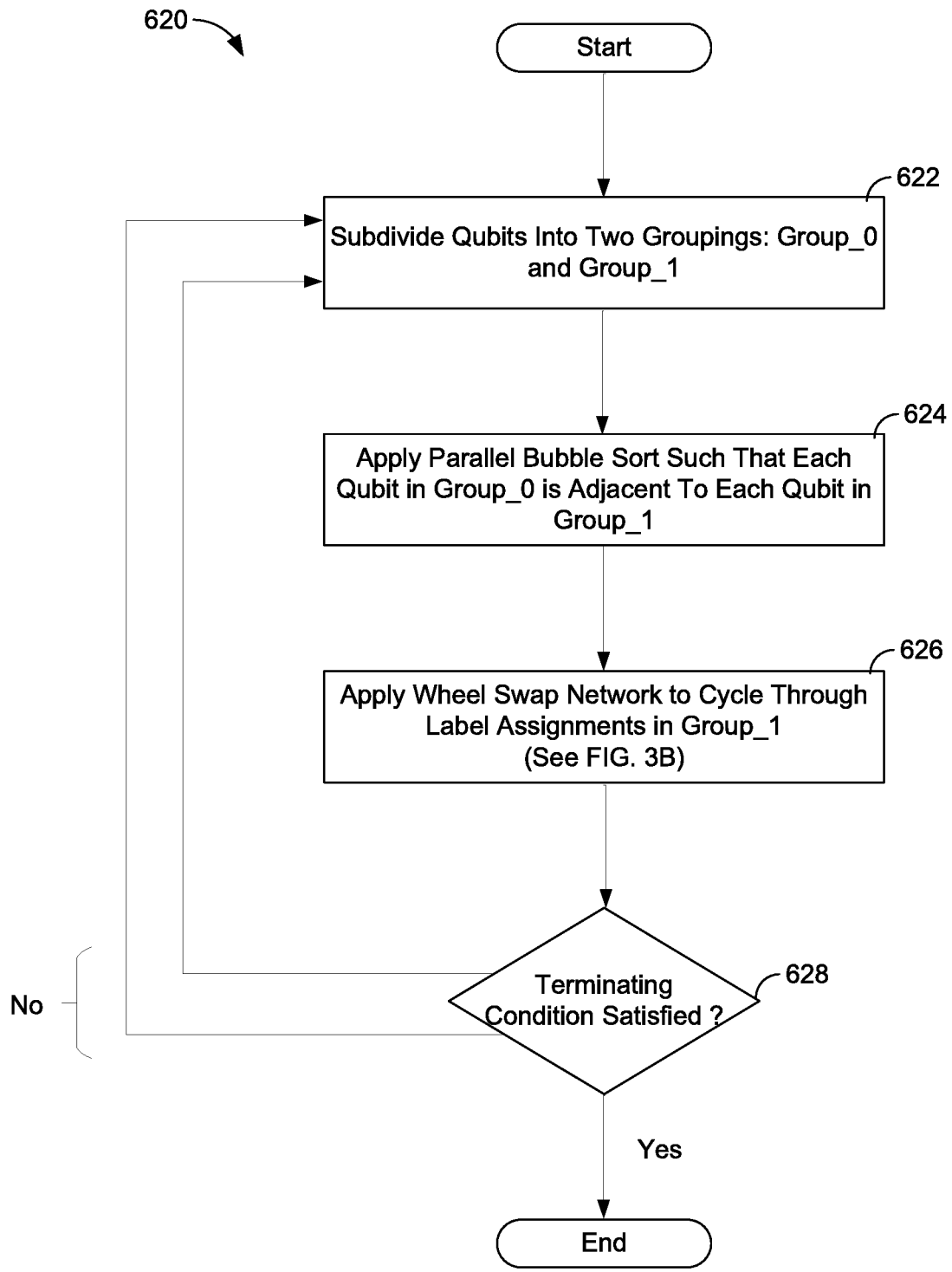
FIG. 6B provides a table that illustrates vectorizations of a configuration for 4-qubit combinations, where $5 \leq N \leq 10$ that are consistent with the various embodiments presented herein.

FIG. 6B provides a table 610 that illustrates vectorizations of a 4-qubit configuration for 5≤N≤10 that is consistent with the various embodiments presented herein. Each row of table 610 corresponds to a separate value of N, where the value of N is indicated in the first column. The second, third, fourth, and fifth columns of table 410 correspond to the category 1, category 2 (as well as categories 3 and 4), category 5 (as well as categories 6-10), and category 11 (as well as categories 12-14) of 4-qubit combination types. Each entry in the table provides a vector (of length N) for the corresponding value of N and combination type category. As will be discussed below, the vector indicates an arrangement of combination types to achieve each of the $$\binom{N}{4}$$

4-qubit interactions.

FIG. 6C provides a flow diagram that illustrates a process 620 of swap operations implemented by a 2-qubit slot network employed for 4-qubit embodiments discussed herein. As will be discussed below, 2-qubit slot network, such as the one implemented via process 620, is employed to generate 4-qubit interactions, such as categories 2, 3, and 4 combination type interactions of table 600 of FIG. 6A. Similar with the other processes discussed throughout, even though the discussion of process 620 is directed toward qubit swap operations, the embodiments are not so limited, and the swap operations may be applied to fermionic orbitals. Process 620 may be a recursive process. Process 620 begins, after a start block, at block 622, where the qubits (or fermionic orbitals) are divided into two groups: group_0 and group_1. The qubits may be members of a wheel. If the wheel has n qubits, then group_0 may include $$\left\lfloor \frac{n}{2} \right\rfloor$$

qubits and group_1 may include $$\left\lceil \frac{n}{2} \right\rceil$$

qubits.

At block 624, a parallel bubble sort is applied such that the qubits in each group are adjacent to the qubits with corresponding indices in the other group. At block 626, a wheel swap network is applied to cycle through the label assignments in group_1. At decision block 628, it is determined if the terminating condition has been met. In some embodiments, the terminating condition for process 620 may include whether $$\left\lfloor \frac{n}{2} \right\rfloor \geq 2.$$

If the terminating condition is met, then process 620 may terminate. Otherwise, process 620 may return to block 622 for a recursive call of process 620. The double return arrows indicate that each of group_0 and group_1 recursively call process 620. In the recursive call, each group is further sub-divided, reducing the current value of n in each recursive call. Note that such with other embodiments, the number of recursive calls is deterministic, thus the decision block 628 may not need to be invoked. It can be shown that the circuit depth of a 2-qubit slot network that implements process 620 is:

$$d_s(n) \leq \frac{5}{2}n + 7\log_2\left(\left\lceil \frac{n}{2} \right\rceil\right) + 14.$$

As noted in table 600 of FIG. 6A, this swap network depth is employed in category 1, 2, and 3 qubit combinations.

Figure 7A:
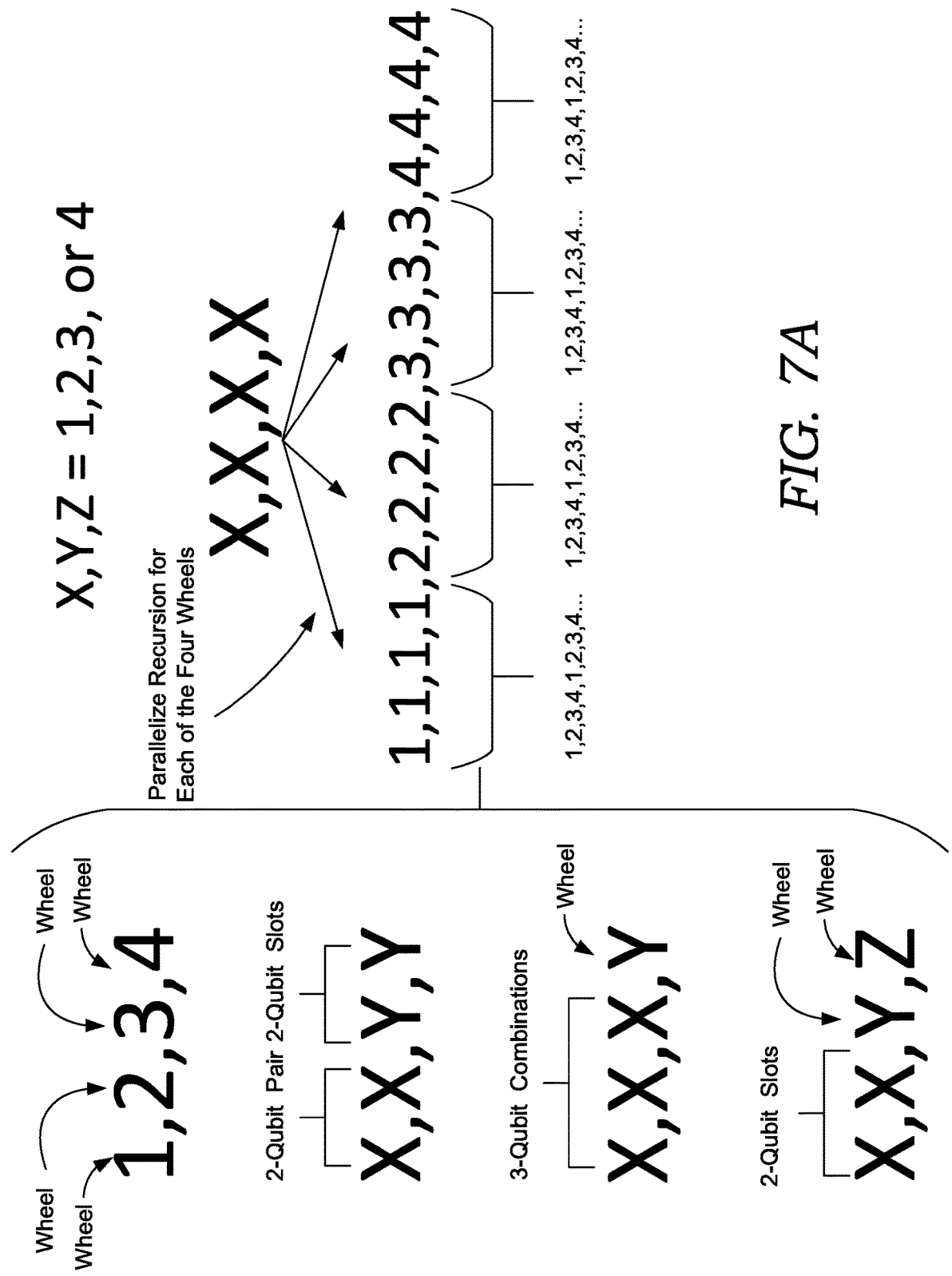
FIG. 7A shows an overview of the types of swap operations employed in at least one embodiment to generate the localized 4-qubit combinations.

FIG. 7A provides a schematic overview of the combination of swap networks to localize each type of 4-qubit combinations. More specifically, FIG. 7A shows an overview of the types of swap operations employed in at least one embodiment to generate the localized 4-qubit combinations for: 1234, XXYY, XXYZ, XXXY, and XXXX combinations types. As shown, for 1,2,3,4 types, four instances of wheel swap networks are employed, where each of the 1, 2, 3, and 4 class of qubits are included in one of the wheels. Similar to 3-qubit combinations, the rotation of the wheels is nested and may be run as multiple nested subroutines. Process 720 of FIG. 7C shows one non-limiting embodiment of the nesting. For XXYY types, a 2-qubit pair swap network is utilized for each of the X wheels and a 2-qubit slot swap network is employed for each of the Y wheels. For the XXXY types, a 3-qubit combination swap network is employed for each of the X wheels and a wheel swap network is employed for each of the Y wheels. For XXYZ types, a 2-qubit slot swap network is employed for each of the X wheels, a wheel swap network is employed for each of the Y wheels, and a wheel swap network is employed for each of the Z wheels. As also shown in FIG. 7A, the XXXX combinations are generated from recursive calls to the other types of combinations. Recursive calls are performed for each for the wheel. Thus, four sub-wheels are generated for wheel_1 (e.g., wheel_1_1, wheel_1_2, wheel_1_3, and wheel_1_4), four sub-wheels are generated for wheel_2 (e.g., wheel_2_1, wheel_2_2, wheel_2_3, and wheel_2_4), four sub-wheels are generated for wheel_3 (e.g., wheel_3_1, wheel_3_2, wheel_3_3, and wheel_3_4), and four sub-wheels are generated for wheel_4 (e.g., wheel_4_1, wheel_4_2, wheel_4_3, and wheel_4_4). The recursion is terminated when each of the 1111, 2222, 3333, and 4444 type localized combinations have been generated. The recursive calls for each wheel (and each sub-wheel may be parallelized to decrease the required circuit depth.

Figure 7B:
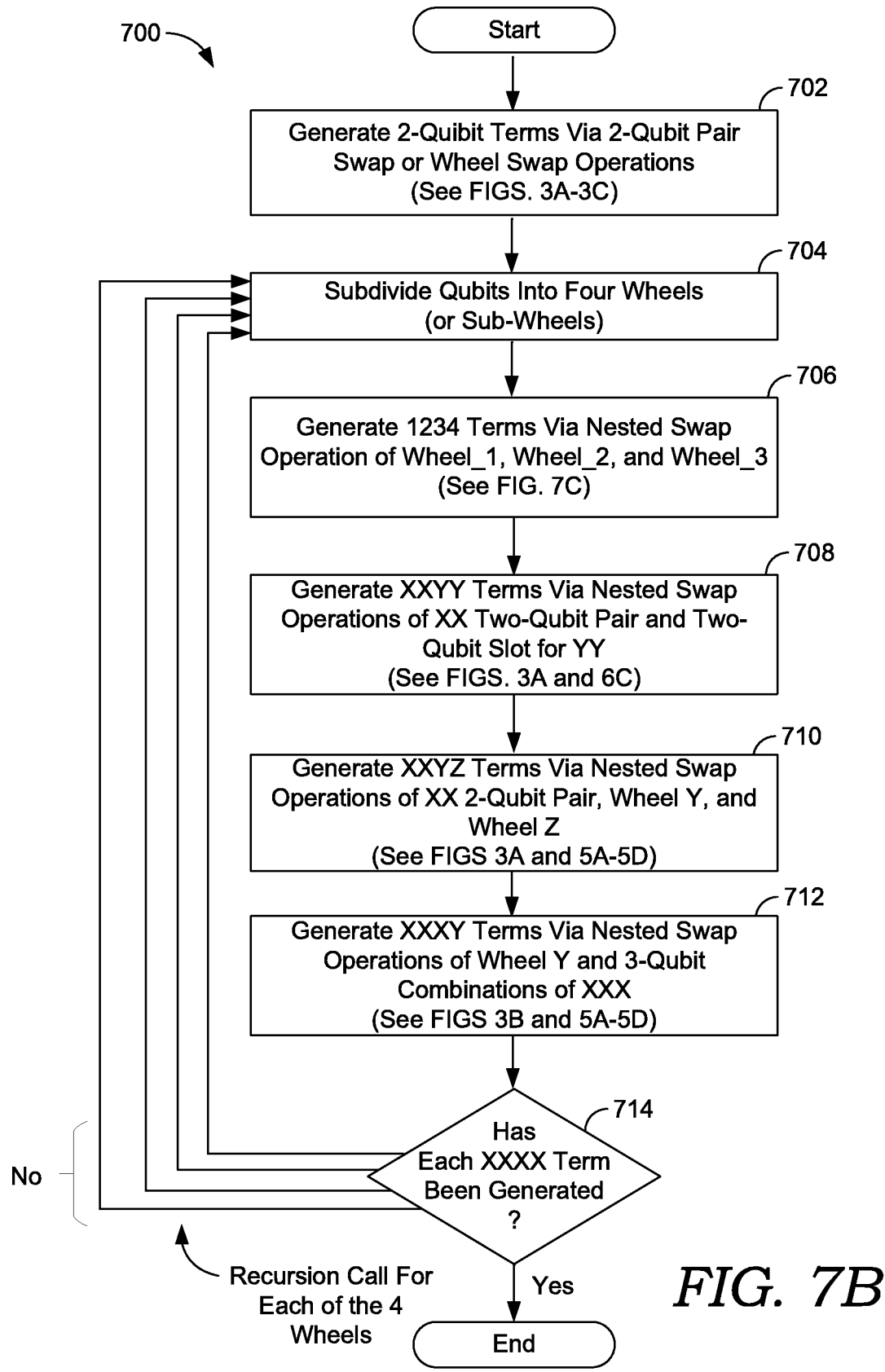
FIG. 7B provides a flow diagram that illustrates a process to localize all 4-qubit combinations within a quantum computer.
Figure 7C:
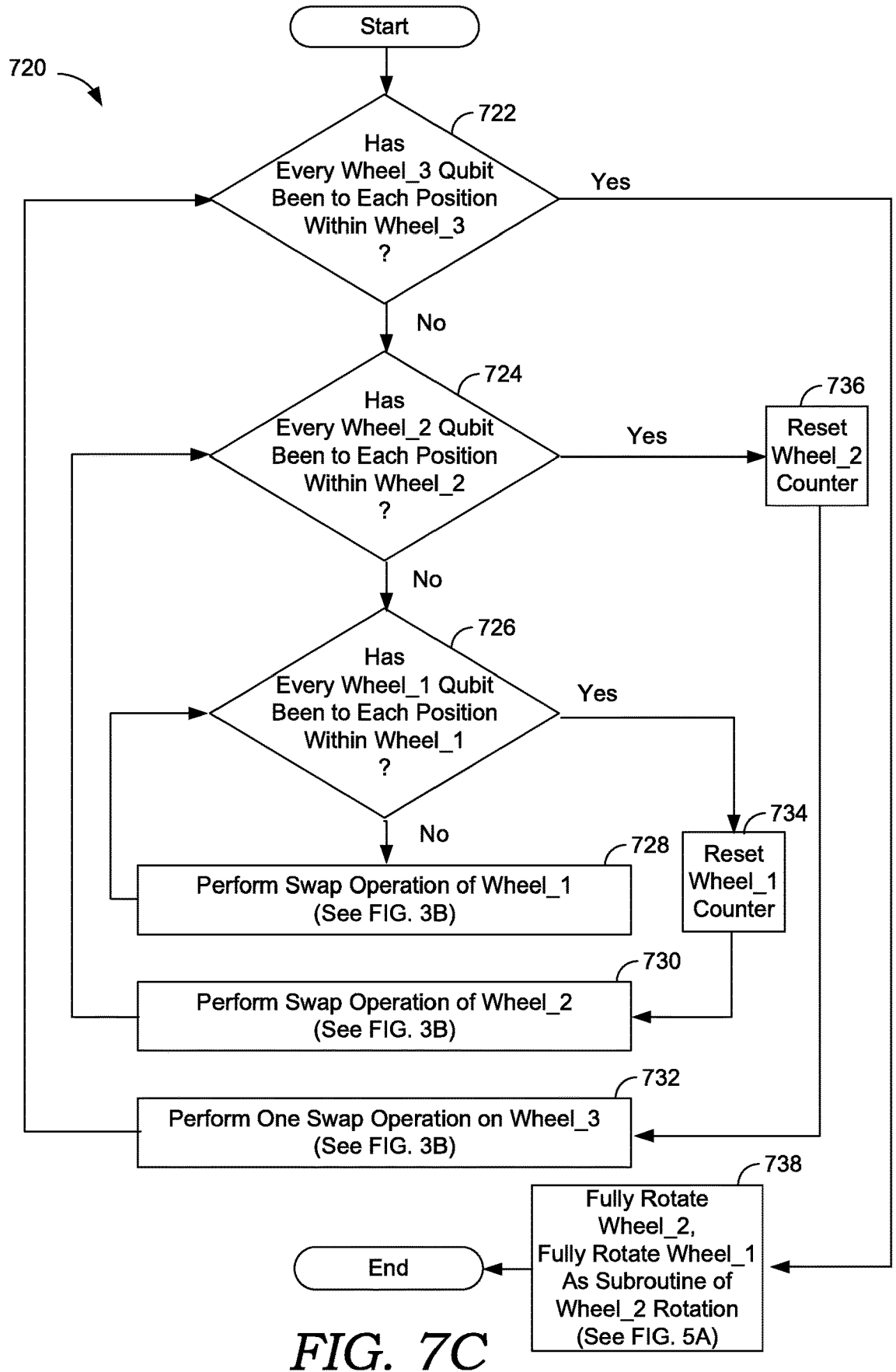
FIG. 7C provides a flow diagram that illustrates a process to localize all category 0 4-qubit combinations within a quantum computer.
Figure 7D:
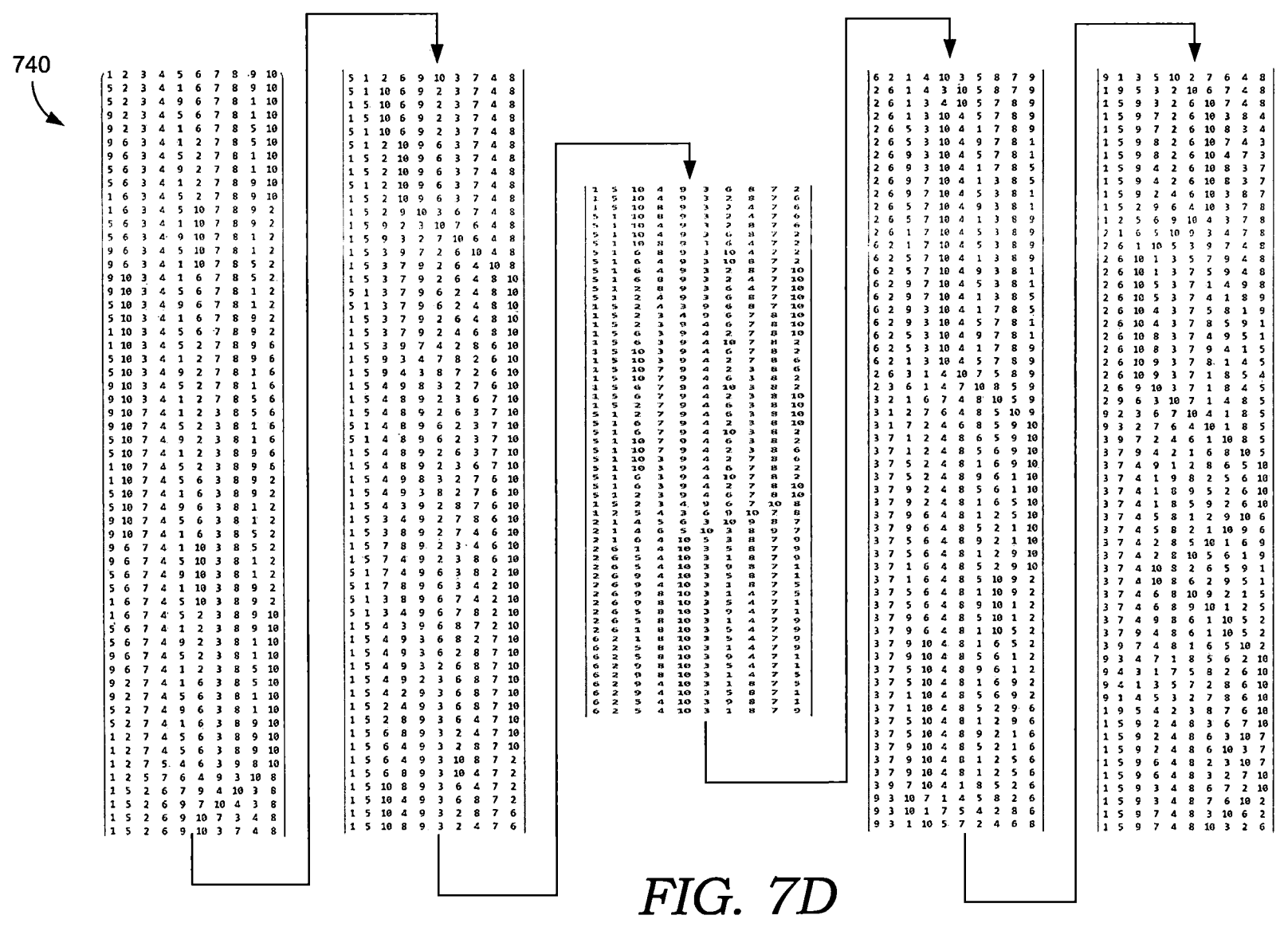
Figure 7E:
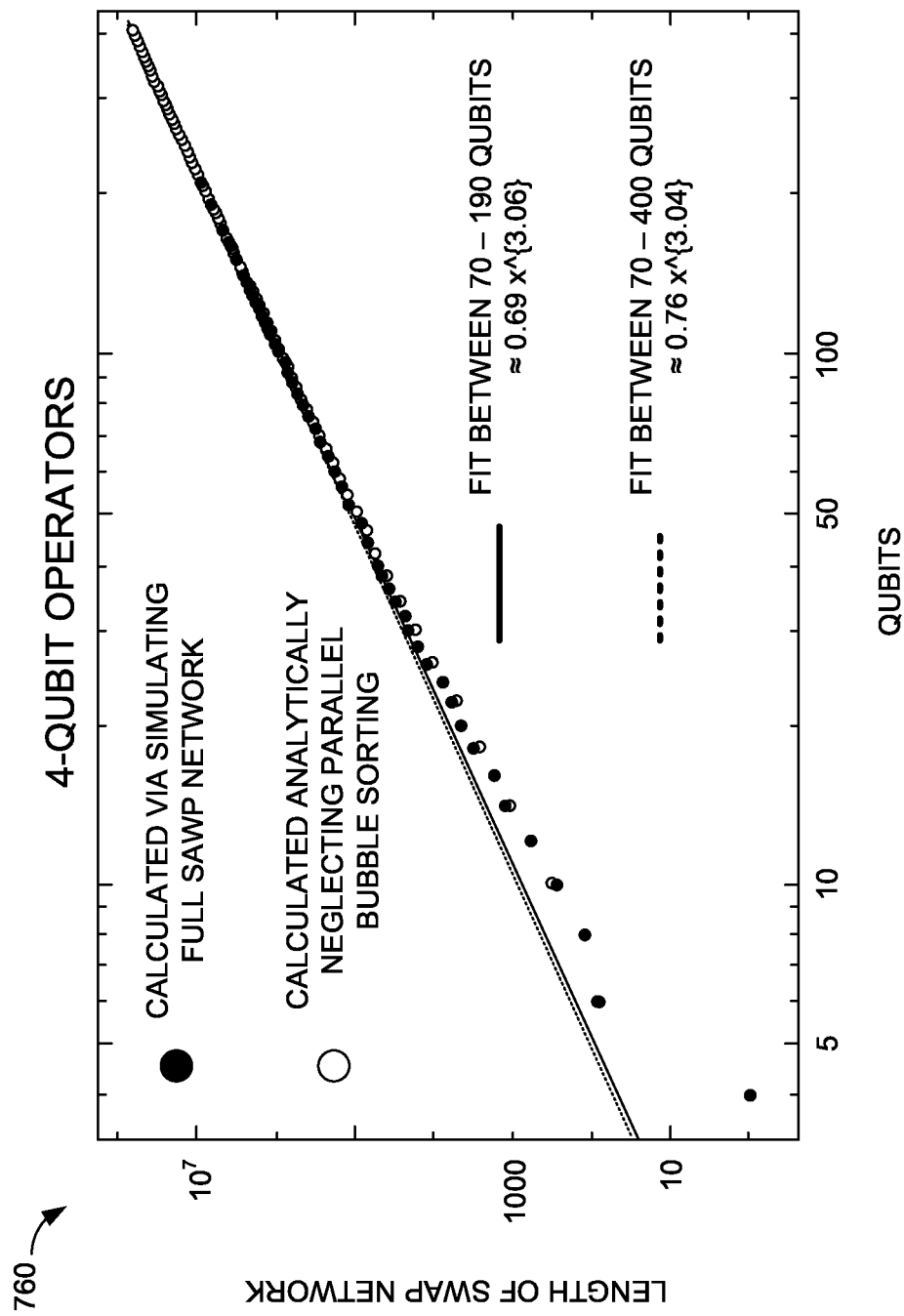
FIG. 7E provides a plot of numerical results indicating that the circuit depth for a swap network for 4-qubit operators scales approximately as $\mathcal{O}(N^3)$.

FIG. 7B provides a flow diagram that illustrates a process 700 to localize all of the 2-qubit and all of the 4-qubit combinations within a quantum computer. More specifically, process 700 uses the swap networks for each of the combination types illustrated in FIG. 7A. Process 700 starts, after a start block, at block 702, where each of the each of the 2-qubit terms are generated by either a 2-qubit pair network or a wheel swap network applied to the register. The networks may perform a plurality of swap operations on the register. Various embodiments of 2-qubit pair and wheel swap operations are discussed at least in conjunction for FIGS. 3A-3C. At block 704, the qubits are subdivided into four wheels: wheel_1, wheel_2, wheel_3, and wheel_4. At discussed throughout, the qubits included in wheel_4 need not be swapped. Thus, wheel_4 may not need to be generated in some embodiments, and the qubits belonging to wheel_4 may be classified as not belonging to anyone of wheel_1, wheel_2, or wheel_3.

At block 706, the 1234 type localized combinations are generated via a wheel swap operations applied by a wheel swap network for each of the four wheels. The wheel swap operations may be nested, similar, to process 500 of FIG. 5A. One non-limiting embodiment of nesting the wheel swap operations is discussed in conjunction with process 720 of FIG. 7C. Thus, at block 704, each of the category 1 (as illustrated in table 600 of FIG. 7C) is generated. As shown in table 600, for category 1 the depth of the swap operations may be deterministically determined via $d_w(n)$.

At block 708, the XXYY terms are generated via nested swap operations of a 2-qubit pair swap network applied to the X wheels and 2-qubit slot networks are applied to the Y wheels. Various embodiments of these swap operations are discussed in conjunction with at least FIGS. 3A and 6C. Thus, at block 708, each of the combinations for categories 2, 3, and 4 of table 600 is generated. As shown in table 600, for categories 2, 3, and 4, the depth of the swap operations may be deterministically determined via $d_w(n)$ and $d_s(n)$. Note that prior to generating the XXYY terms at block 708, a sorting of the qubits may be performed to configure the qubits in an appropriate vectorized order. Various embodiments for of 4-qubit vectorizations are shown in table 610 of FIG. 6B. For example, a parallel bubble sorting swap operation may be performed.

At block 710, the XXYZ terms are generated by the swap operations of a 2-qubit pair swap network operating on the X wheels and a wheel swap network operating on each of the Y and Z wheels (e.g., see FIGS. 3B and 5A-5D). that is, the category 5-10 combinations of table 600 are generated at block 710. As shown in table 610, for categories 5-10, the depth of the swap operations may be deterministically determined via $d_2(n)$ and $d_w(n)$ applied to the appropriate wheels. Similar to above, a parallelized bubble sort may be performed on the qubits to properly sort the qubits via the appropriate vectorized ordering.

At block 712, the XXXY terms are generated via the swap operations of a wheel swap network applied to the Y wheels and a 3-qubit swap network applied to the X wheels. That is, the category 11-14 combinations are generated at block 712. More specifically, the 3-qubit constructions are employed to cycle through each of the triple pairs and then the wheel is used to cycle through the unpaired index Various embodiments for such swap operations are discussed in conjunction with at least FIGS. 3B and 5A-5D. As shown in table 610, for categories 11-14, the depth of the swap operations may be deterministically determined via $d_3(n)$ and $d_w(n)$ applied to the appropriate wheels Note that prior to generating the XXXY terms at block 712, a sorting of the qubits may be performed to configure the qubits in an appropriate vectorized order. For example, a parallel bubble sorting swap operation may be performed.

For the generation of category 15 combinations, a recursive process, similar to the category 4 combinations for 3-qubits is employed. A parallel bubble swap may be employed to order the qubits into the appropriate qubit vector. At decision block 714, it is determined whether each of the XXXX type combinations has been localized. If so, then process 700 terminates. Otherwise, a recursion call is made for each of the four wheels. That is, each wheel is returned to block 704. The recursion calls for the four wheel are shown via the four return paths from block 714 to block 704. Similar to the discussion in regards to the decision blocks of processes 300, 320, 500, and 580 of FIGS. 3A, 3B, 5A, and 5C respectively, decision block 714 need not be implemented in the various embodiments due to the deterministic swap depths required to satisfy the loop's terminating condition.

FIG. 7C provides a flow diagram that illustrates a process 720 to localize all category 0 (i.e., 1234 type combinations) 4-qubit combinations within a quantum computer. Process 720 may be a subroutine of process 700 of FIG. 7B. For example, process 720 may be called via an execution of block 706 of process 700. In process 720, parallelized swap operations are performed (via a wheel swap network) on wheel_3, such that each qubit in wheel_3 visits each position in wheel_3. That is, wheel_3 is fully rotated through its depth. Wheel_2 is fully rotated through its depth as a subroutine of the rotation of wheel_3. Wheel_1 is fully rotated through its depth as a subroutine of the rotation of wheel_2. To generate the category 0 combinations, wheel_4 need not be rotated. Thus, is somewhat similar to process 500 of FIG. 5A, but involves four wheels, rather than three wheels.

For illustrative purposes, and because the notion that wheels are being rotated, via nested rotations and/or subroutines, the concept of wheel counters has been introduced in process 720. These wheel counters may be considered similar to a loop counter (or loop index) in a for-loop process. Because the loops of process 720 are run as subroutines, these wheel counters are incremented and reset once a nested loop has completed. The incrementing of the wheel counters is inferred and process 720 includes explicit blocks to reset the wheel counters (e.g., block 734 and 736). Note that these wheel (or loop) counters are for illustrative purposes only, and need not be implemented due to the deterministically determinable depth of the swap operations. Furthermore, similarly to as discussed above, the decision blocks (e.g., blocks 722, 724, and 726) that check for the terminating condition of the loops need not be explicitly implemented due to the deterministic-nature of the swap operations, Process 720 begins, after a start block, at decision block 722, where it is determined whether each qubit in wheel_3 has visited each position in wheel_3 at least once. If the terminating condition for wheel_3 is satisfied, process 720 flows to block 738. At block 738, wheel_2 is fully rotated one more time and wheel_1 is rotated as a subroutine of the rotation of wheel_2. One embodiment for rotating wheel_1 as a subroutine of fully rotating wheel_2 is discussed in conjunction with at least process 500 of FIG. 5A. These final rotations of wheel_1 and wheel_2 will complete the generation of all the 1234 type combinations. Thus, process 720 may terminate after the execution of block 738. If the terminating condition for wheel_3 is not satisfied, then process 720 flows to decision block 724.

At decision block 724, it is determined whether each qubit in wheel_2 has visited each position in wheel_2, since a counter for wheel_2 has been reset. If the terminating condition for wheel_2 is satisfied, process 720 flows to block 736, otherwise process flows to decision block 726. At block 736, the counter for wheel_2 is reset, and process 720 flows to block 732. At block 732, one parallelized swap operation is performed on wheel_3. Various embodiments for performing a parallelized swap operation on a wheel are discussed in conjunction with at least process 320 of FIG. 3B. However, briefly here, wheel_3 is rotated via an odd-paired or an even-paired parallelized qubit swap operation. Process 720 then returns back to decision block 722.

At decision block 726, it is determined whether each qubit in wheel_1 has visited each position in wheel_1, since a counter for wheel_1 has been reset. If the terminating condition for wheel_1 is satisfied, process 720 flows to block 734, otherwise process flows to block 728. At block 734, the counter for wheel_1 is reset, and process 720 flows to block 730. At block 730, one parallelized swap operation is performed on wheel_2. Various embodiments for performing a parallelized swap operation on a wheel are discussed in conjunction with at least process 320 of FIG. 3B. However, briefly here, wheel_2 is rotated via an odd-paired or an even-paired parallelized qubit swap operation. Process 720 then returns back to decision block 724.

At block 728, one parallelized swap operation is performed on wheel_1. Various embodiments for performing a parallelized swap operation on a wheel are discussed in conjunction with at least process 320 of FIG. 3B. However, briefly here, wheel_1 is rotated via an odd-paired or an even-paired parallelized qubit swap operation. Process 720 then returns back to decision block 726.

FIG. 7D shows the swap operations 740 of the process 700 of FIG. 7B for an N=10 qubit quantum computer. More specifically, swap operations 740 show how each of the possible 4-qubit combinations are localized. The arrows between the columns show the ordering, where the matrix is broken up to fit on a single page.

FIG. 7E provides a plot 760 of calculations indicating that the circuit depth for a swap network for 4-qubit operators scales approximately as $\mathcal{O}(N^3)$. For the solid circular discrete data points (•), the depth of the network, as a function of N, was calculated by simulating the swap operations with a full swap network that included the parallel bubble sort operations required to transition between the swap operations for the various categories of combination types. That is, for the solid data points, the swap operations discussed in conjunction with at least FIGS. 7A-7D, have been numerically simulated to generate each of the localized (i.e., logically consecutive in the register) 4-qubit pairs of the possible $$\binom{N}{4}$$

pairings for up to N=400. For the non-solid data points (○), the depth of the network was determined analytically, via expressions for the depth of swap operations required by the various categories shown in the fifth column of table 600 of FIG. 6A. For the non-solid data points, the contribution of the parallel bubble sort operations has been neglected. The solid line indicates a log-log linear regression fit to the solid data points. The hashed line indicates a log-log linear regression fit to the non-solid data points. For the solid line, the log-log linear fit is: $(0.69\pm0.09)\cdot10^{3.06\pm0.03}$. For the hashed line, the log-log linear fit is: $(0.76\pm0.03)\cdot10^{3.04\pm0.01}$. The linear fits to both methods (numerical simulation and analytic calculations) demonstrates that the depth of the swap network (or parallelized swap operations) scales as approximately $\mathcal{O}(N^3)$, and that the parallel bubble sorts do not drive the scaling of the required circuit depth.

FIG. 7E provides a plot 760 of numerical results indicating that the circuit depth for a swap network for 4-qubit operators scales approximately as $\mathcal{O}(N^3)$. The swap operations discussed in conjunction with at least FIGS. 7A-7D, have been numerically simulated to generate each of the localized (i.e., logically consecutive in the register) 4-qubit pairs of the possible $$\binom{N}{4}$$

pairings for up to N=400. Note that plot 760 is a log-log plot. A log-log regression fit shows that the depth of the swap network (or parallelized swap operations) scales as approximately $\mathcal{O}(N^3)$. Thus, the various enhanced embodiments provide at least an order magnitude reduction in the circuit depth, as compared to conventional methods, which scale approximately as $\mathcal{O}(N^4)$.

Quantum Computing Environment

Figure 8:
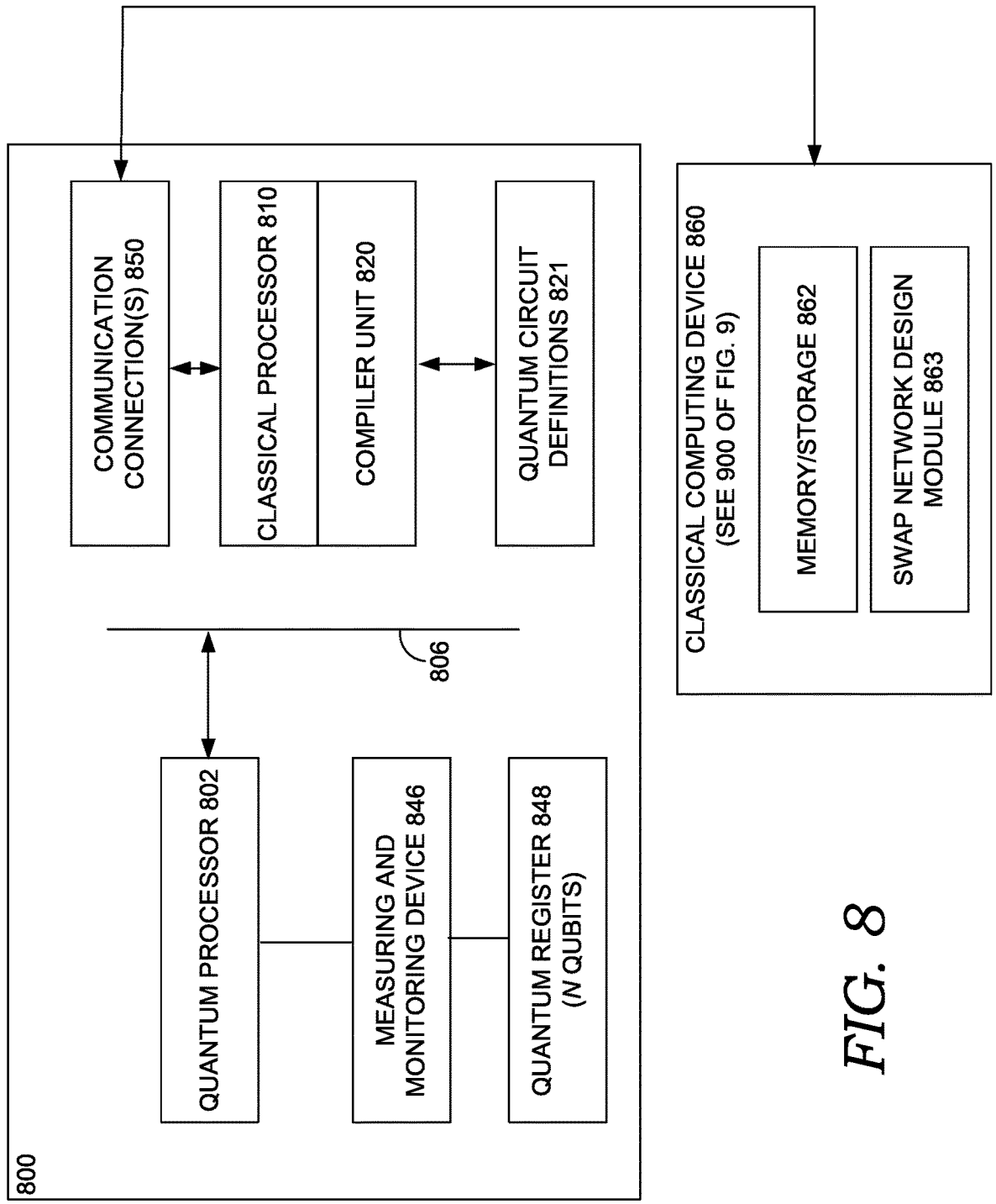
FIG. 8 is a block diagram of an exemplary quantum computing environment suitable for use in implementing an embodiment of the present disclosure.

FIG. 8 is a block diagram of an exemplary quantum computing environment 800 suitable for use in implementing embodiments of the present disclosure. Quantum computing environment 800 includes quantum hardware, such as but not limited to a quantum processing unit 802, quantum register, and one or more monitoring/measuring device(s) 846. Quantum register 848 may include physical implementations of N qubits. The qubits may be monitored, measured, observed, or otherwise probed via measuring and monitoring device 846. The quantum processor 802 executes quantum circuits (e.g., circuits implementing the time-evolution operators and parallelized swap networks discussed herein). The circuits may be precompiled by classical compiler unit 820 using one or more classical processor(s) 810. The compiled quantum circuits may be downloaded into the quantum processing unit via quantum bus 806. In some cases, quantum circuits or portions thereof are predefined and stored as quantum circuit definitions in a devices memory 821. For example, quantum circuits associated with second quantization representations of Hamiltonians, as well as quantum circuits implementing qubit swap networks, applied as described above, or other functions and procedures or portions thereof can be stored in a library. A classical computer 860 can be arranged to control a quantum computer or one or more quantum circuits thereof. The classical computer 860 can receive the output of a classical or quantum computer. Based on the received output, the classical computer indicates which quantum circuits are to be used in subsequent quantum computations, provides definitions of suitable quantum circuits, or, in some cases, and controls additional classical computations. The specific architecture depends on the number of qubits, as well as other design considerations. Accordingly, a swap network design module 863 may at least partially automate some of the design work to arrive at the swap network definitions, based on one or more design parameters and/or design criteria. Various embodiments of a classical computing device and/or a classical computing environment are discussed in conjunction with at least FIG. 9.

With reference to FIG. 8, the compilation of quantum circuits may include the process of translation of a high-level description of a quantum algorithm into a sequence of quantum circuits. Such high-level description may be stored, as the case may be, on one or more external computer(s) 860 outside the quantum computing environment 800 utilizing one or more memory and/or storage device(s) 862, then downloaded as necessary into the computing environment 800 via one or more communication connection(s) 850. The high-level description can be stored and interpreted classically, and a classical computer can control the sequence of gates defined in a quantum computer. The high level description also controls application of gates based on initial, intermediate, or final data values. In one example, a memory and/or storage device 862 stores computer executable instructions for coefficient ordering and adjustment as described above. Such instructions can also be provided to the classical processor 810.

Classical Computing Device

Figure 9:
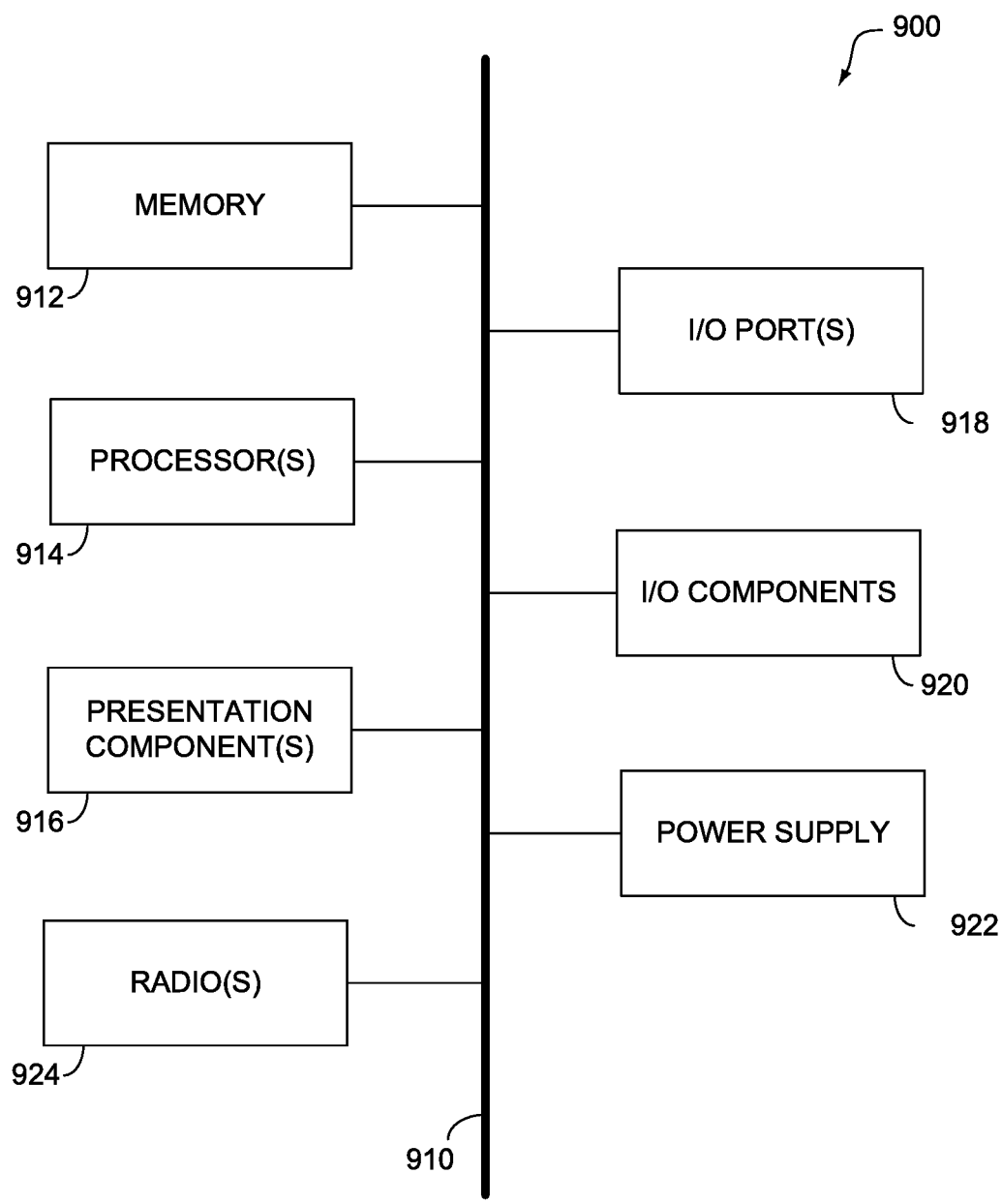
FIG. 9 is a block diagram of an exemplary classical computing environment suitable for use in implementing an embodiment of the present disclosure.

With reference to FIG. 9, classical computing device 900 includes a bus 910 that directly or indirectly couples the following devices: memory 912, one or more processors 914, one or more presentation components 916, one or more input/output (I/O) ports 918, one or more I/O components 920, and an illustrative power supply 922. As discussed in conjunction with FIG. 8, classical computing device 900 may be employed on the quantum computing environment 800 of FIG. 8. Bus 910 represents what may be one or more busses (such as an address bus, data bus, or combination thereof). Although the various blocks of FIG. 9 are shown with lines for the sake of clarity, in reality, these blocks represent logical, not necessarily actual, components. For example, one may consider a presentation component such as a display device to be an I/O component. Also, processors have memory. The inventors hereof recognize that such is the nature of the art and reiterate that the diagram of FIG. 9 is merely illustrative of an exemplary computing device that can be used in connection with one or more embodiments of the present disclosure. Distinction is not made between such categories as "workstation," "server," "laptop," "handheld device," etc., as all are contemplated within the scope of FIG. 9 and with reference to "computing device."

Computing device 900 typically includes a variety of computer-readable media. Computer-readable media can be any available media that can be accessed by computing device 900 and includes both volatile and nonvolatile media, removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage devices, or any other medium which can be used to store the desired information and which can be accessed by computing device 900. Computer storage media does not comprise signals per se. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. Combinations of any of the above should also be included within the scope of computer-readable media.

Memory 912 includes computer storage media in the form of volatile and/or nonvolatile memory. The memory may be removable, non-removable, or a combination thereof. Exemplary hardware devices include solid-state memory, hard drives, optical-disc drives, etc. Computing device 900 includes one or more processors 914 that read data from various entities such as memory 912 or I/O components 920. Presentation component(s) 916 presents data indications to a user or other device. In some implementations, presentation component 220 of system 200 may be embodied as a presentation component 916. Other examples of presentation components may include a display device, speaker, printing component, vibrating component, and the like.

The I/O ports 918 allow computing device 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, touch and stylus recognition, facial recognition, biometric recognition, gesture recognition both on screen and adjacent to the screen, air gestures, head and eye tracking, and touch recognition associated with displays on the computing device 900. The computing device 900 may be equipped with depth cameras, such as stereoscopic camera systems, infrared camera systems, RGB camera systems, and combinations of these, for gesture detection and recognition. Additionally, the computing device 900 may be equipped with accelerometers or gyroscopes that enable detection of motion. The output of the accelerometers or gyroscopes may be provided to the display of the computing device 900 to render immersive augmented reality or virtual reality.

Some embodiments of computing device 900 may include one or more radio(s) 924 (or similar wireless communication components). The radio 924 transmits and receives radio or wireless communications. The computing device 900 may be a wireless terminal adapted to receive communications and media over various wireless networks. Computing device 900 may communicate via wireless protocols, such as code division multiple access ("CDMA"), global system for mobiles ("GSM"), or time division multiple access ("TDMA"), as well as others, to communicate with other devices. The radio communications may be a short-range connection, a long-range connection, or a combination of both a short-range and a long-range wireless telecommunications connection. When we refer to "short" and "long" types of connections, we do not mean to refer to the spatial relation between two devices. Instead, we are generally referring to short range and long range as different categories, or types, of connections (i.e., a primary connection and a secondary connection). A short-range connection may include, by way of example and not limitation, a Wi-Fi® connection to a device (e.g., mobile hotspot) that provides access to a wireless communications network, such as a WLAN connection using the 802.11 protocol; a Bluetooth connection to another computing device is a second example of a short-range connection, or a near-field communication connection. A long-range connection may include a connection using, by way of example and not limitation, one or more of CDMA, GPRS, GSM, TDMA, and 802.16 protocols.

Many different arrangements of the various components depicted, as well as components not shown, are possible without departing from the scope of the claims below. Embodiments of the disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims.

What is claimed is:

1. Quantum computing hardware configured to operate on a set of qubits to perform a method, wherein the set of qubits defines a plurality of 4-qubit combinations, the method comprising:

iteratively updating an order of the set of qubits, via a plurality of qubit swap operations, such the each of the plurality of 4-qubit combinations is represented as a consecutive 4-qubit grouping within the order of the set of qubits, at least once during the plurality of swap operations to generate a plurality of consecutive 4-qubit groupings.

2. The quantum computing hardware of claim 1, wherein the set of qubits further defines a plurality of 2-qubit combinations and the method further comprises:

iteratively updating the order of the set of qubits, via a second plurality of qubit swap operations, such the each of the plurality of 2-qubit combinations is represented as a consecutive 2-qubit grouping within the order of the set of qubits, at least once during the second plurality of swap operations to generate a plurality of consecutive 2-qubit groupings.

3. The quantum computing hardware of claim 1, wherein each pair of qubits swapped in each of the plurality of swap operations is separated by at most three qubits within the order of the set of qubits.

4. The quantum computing hardware of claim 1, the method further comprising:
  subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets; and
  performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the second subset of qubits, a third qubit from the third subset of qubits, and a fourth qubit from the fourth subset of qubits.

5. The quantum computing hardware of claim 4, wherein performing the portion of the plurality of qubit swap operations comprises:
  performing a plurality of third wheel nearest-neighbor qubit swaps, such that each qubit of the third subset of qubits is positioned at each position of the third wheel at least once;
  in response to performing a third wheel nearest-neighbor qubit swap of the plurality of third wheel nearest-neighbor qubit swaps, performing a plurality of second wheel nearest-neighbor qubit swaps, such that each qubit of the second subset of qubits is positioned at each position of the second wheel at least once; and
  in response to performing a second wheel nearest-neighbor qubit swap of the plurality of second wheel nearest-neighbor qubit swaps, performing a plurality of first wheel nearest-neighbor qubit swaps, such that each qubit of the first subset of qubits is positioned at each position of the first wheel at least once.

6. The quantum computing hardware of claim 1, the method further comprising:
  subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;
  iteratively updating the order of the set of qubits, via a first portion of the plurality of qubit swap operation, to generate a vectorization of the set of qubits that corresponds to an instance of a wheel of a network of quantum gates and an instance of a 2-slot swap network of the network of quantum gates; and
  employing the instance of the 2-qubit swap network and the instance of the 2-qubit slot swap network and based on the vectorization of the set of qubits, performing a second portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, and a second qubit from the first subset of qubits, a third qubit from the second subset of qubits, and a fourth qubit from the second subset of qubits.

7. The quantum computing hardware of claim 1, the method further comprising:
  subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;
  iteratively updating the order of the set of qubits, via a first portion of the plurality of qubit swap operation, to generate a vectorization of the set of qubits that corresponds to an instance of a wheel swap network of the network of quantum gates and an instance of a 3-qubit swap network of a network of quantum gates; and
  employing the instance of the wheel swap network and the instance of the 3-qubit swap network and based on the vectorization of the set of qubits, performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the first subset of qubits, a third qubit of the first subset of qubits, and a fourth qubit from the second subset of qubits.

8. The quantum computing hardware of claim 1, the method further comprising:
  subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;
  performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the first subset of qubits, a third qubit of the first subset of qubits, and a fourth qubit from the first subset of qubits.

9. A quantum computing system that comprises:
  a quantum register that includes a plurality of qubits that defines a plurality of 4-qubit combinations; and
  quantum hardware that is configured to execute a network of quantum gates that operates on the set of qubits to perform a method comprising:
  iteratively updating an order of the set of qubits, via a plurality of qubit swap operations, such the each of the plurality of 4-qubit combinations is represented as a consecutive 4-qubit grouping within the order of the set of qubits, at least once during the plurality of swap operations to generate a plurality of consecutive 4-qubit groupings.

10. The quantum computing system of claim 9, wherein the set of qubits further defines a plurality of 2-qubit combinations and the method further comprises:

iteratively updating the order of the set of qubits, via a second plurality of qubit swap operations, such the each of the plurality of 2-qubit combinations is represented as a consecutive 2-qubit grouping within the order of the set of qubits, at least once during the second plurality of swap operations to generate a plurality of consecutive 2-qubit groupings.

11. The quantum computing system of claim 9, wherein each pair of qubits swapped in each of the plurality of swap operations is separated by at most three qubits within the order of the set of qubits.

12. The quantum computing system of claim 9, the method further comprising:
subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets; and
performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the second subset of qubits, a third qubit from the third subset of qubits, and a fourth qubit from the fourth subset of qubits.

13. The quantum computing system of claim 12, wherein performing the portion of the plurality of qubit swap operations comprises:
performing a plurality of third wheel nearest-neighbor qubit swaps, such that each qubit of the third subset of qubits is positioned at each position of the third wheel at least once;
in response to performing a third wheel nearest-neighbor qubit swap of the plurality of third wheel nearest-neighbor qubit swaps, performing a plurality of second wheel nearest-neighbor qubit swaps, such that each qubit of the second subset of qubits is positioned at each position of the second wheel at least once; and
in response to performing a second wheel nearest-neighbor qubit swap of the plurality of second wheel nearest-neighbor qubit swaps, performing a plurality of first wheel nearest-neighbor qubit swaps, such that each qubit of the first subset of qubits is positioned at each position of the first wheel at least once.

14. The quantum computing system of claim 9, the method further comprising:
subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;
iteratively updating the order of the set of qubits, via a first portion of the plurality of qubit swap operation, to generate a vectorization of the set of qubits that corresponds to an instance of a wheel of the network of quantum gates and an instance of a 2-slot swap network of the network of quantum gates; and
employing the instance of the 2-qubit swap network and the instance of the 2-qubit slot swap network and based on the vectorization of the set of qubits, performing a second portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, and a second qubit from the first subset of qubits, a third qubit from the second subset of qubits, and a fourth qubit from the second subset of qubits.

15. The quantum computing system of claim 9, the method further comprising:
subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;
iteratively updating the order of the set of qubits, via a first portion of the plurality of qubit swap operation, to generate a vectorization of the set of qubits that corresponds to an instance of a wheel swap network of the network of quantum gates and an instance of a 3-qubit swap network of the network of quantum gates; and
employing the instance of the wheel swap network and the instance of the 3-qubit swap network and based on the vectorization of the set of qubits, performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the first subset of qubits, a third qubit of the first subset of qubits, and a fourth qubit from the second subset of qubits.

16. A method implemented by a quantum computing device that includes a set of qubits defining a plurality of 4-qubit combinations, the method comprising:
iteratively updating an order of the set of qubits, via a plurality of qubit swap operations, such the each of the plurality of 4-qubit combinations is represented as a consecutive 4-qubit grouping within the order of the set of qubits, at least once during the plurality of swap operations to generate a plurality of consecutive 4-qubit groupings.

17. The method of claim 16, wherein the set of qubits further defines a plurality of 2-qubit combinations and the method further comprises:
iteratively updating the order of the set of qubits, via a second plurality of qubit swap operations, such the each of the plurality of 2-qubit combinations is represented as a consecutive 2-qubit grouping within the order of the set of qubits, at least once during the second plurality of swap operations to generate a plurality of consecutive 2-qubit groupings.

18. The method of claim 16, further comprising:
subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets; and performing a portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, a second qubit from the second subset of qubits, a third qubit from the third subset of qubits, and a fourth qubit from the fourth subset of qubits.

19. The method of claim 18, wherein performing the portion of the plurality of qubit swap operations comprises:

performing a plurality of third wheel nearest-neighbor qubit swaps, such that each qubit of the third subset of qubits is positioned at each position of the third wheel at least once;

in response to performing a third wheel nearest-neighbor qubit swap of the plurality of third wheel nearest-neighbor qubit swaps, performing a plurality of second wheel nearest-neighbor qubit swaps, such that each qubit of the second subset of qubits is positioned at each position of the second wheel at least once; and in response to performing a second wheel nearest-neighbor qubit swap of the plurality of second wheel nearest-neighbor qubit swaps, performing a plurality of first wheel nearest-neighbor qubit swaps, such that each qubit of the first subset of qubits is positioned at each position of the first wheel at least once.

20. The method of claim 16, further comprising:

subdividing the set of qubits into a first qubit wheel, a second qubit wheel, a third qubit wheel, and a fourth qubit wheel, such that the first qubit wheel includes a first subset of the set of qubits, the second qubit wheel includes a second subset of the set of qubits, the third qubit wheel includes a third subset of the set of qubits, and the fourth qubit wheel includes a fourth subset of the set of qubits, wherein the first, second, third, and fourth subsets of qubits are disjoint subsets;

iteratively updating the order of the set of qubits, via a first portion of the plurality of qubit swap operation, to generate a vectorization of the set of qubits that corresponds to an instance of a wheel of a network of quantum gates and an instance of a 2-slot swap network of the network of quantum gates; and employing the instance of the 2-qubit swap network and the instance of the 2-qubit slot swap network and based on the vectorization of the set of qubits, performing a second portion of the plurality of qubit swap operations to generate a portion of the plurality of consecutive 4-qubit groupings, wherein each consecutive 4-qubit grouping of the portion of the plurality of consecutive 4-qubit grouping includes a first qubit from the first subset of qubits, and a second qubit from the first subset of qubits, a third qubit from the second subset of qubits, and a fourth qubit from the second subset of qubits.

* * * * *